(12) United States Patent
Joergensen et al.

(10) Patent No.: US 9,428,558 B2
(45) Date of Patent: Aug. 30, 2016

(54) METHODS FOR PRODUCING SECRETED POLYPEPTIDES

(75) Inventors: Steen Troels Joergensen, Allerød (DK); Anne Breüner, Klampenbor (DK)

(73) Assignee: Novozymes A/S, Bagsvaerd (DK)

( * ) Notice: Subject to any disclaimer, the term of this patent is extended or adjusted under 35 U.S.C. 154(b) by 44 days.

(21) Appl. No.: 14/005,733

(22) PCT Filed: Mar. 22, 2012

(86) PCT No.: PCT/EP2012/055122
§ 371 (c)(1),
(2), (4) Date: Nov. 20, 2013

(87) PCT Pub. No.: WO2012/127001
PCT Pub. Date: Sep. 27, 2012

(65) Prior Publication Data
US 2014/0073009 A1    Mar. 13, 2014

Related U.S. Application Data

(60) Provisional application No. 61/555,870, filed on Nov. 4, 2011.

(30) Foreign Application Priority Data

Mar. 23, 2011 (EP) ..................................... 11159299
Oct. 31, 2011 (EP) ..................................... 11187307

(51) Int. Cl.
| C12N 15/09 | (2006.01) |
| C12N 15/10 | (2006.01) |
| C07K 14/32 | (2006.01) |
| C12N 15/62 | (2006.01) |
| C12N 15/75 | (2006.01) |
| C12P 21/02 | (2006.01) |
| C12N 9/28  | (2006.01) |

(52) U.S. Cl.
CPC .............. *C07K 14/32* (2013.01); *C12N 9/2417* (2013.01); *C12N 15/625* (2013.01); *C12N 15/75* (2013.01); *C12P 21/02* (2013.01); *C07K 2319/02* (2013.01); *Y02P 20/52* (2015.11)

(58) Field of Classification Search
CPC .. C12N 15/00; C12N 15/10; C12N 2511/00; C12N 2800/00
See application file for complete search history.

(56) References Cited

FOREIGN PATENT DOCUMENTS

WO    2011084695 A1    7/2011

OTHER PUBLICATIONS

Ruohonen et al., GenEmbl, database, hit #1, Apr. 1993.*
Degering et al, 2010, Appl Environ Microbiol 76(19), 6370-6376.
Ng et al., Genome Research, vol. 11, pp. 863-874 (2001).

* cited by examiner

*Primary Examiner* — Maryam Monshipouri
(74) *Attorney, Agent, or Firm* — Elias Lambiris

(57) ABSTRACT

The present invention relates to methods for producing a polypeptide comprising using a signal peptide foreign to the polypeptide, nucleic acid constructs comprising a first and a second nucleotide sequence encoding the signal peptide and the polypeptide and expression vectors and host cells comprising said nucleic acid construct. The signal peptide is the LQ2 peptide which is a hybrid of sequence from the signal peptide of alpha amylase from *Bacillus licheniformis* and of alpha amylase from *Bacillus amyloliquefaciens*.

30 Claims, 6 Drawing Sheets

METHODS FOR PRODUCING SECRETED POLYPEPTIDES

CROSS-REFERENCE TO RELATED APPLICATIONS

This application is a 35 U.S.C. 371 national application of PCT/EP2012/055122, filed on Mar. 22, 2012, which claims priority from European application no. 11159299.4, filed on Mar. 23, 2011, European application no. 11187307.1, filed on Oct. 31, 2011, and US provisional application No. 61/555,870, filed on Nov. 4, 2011. The contents of these applications are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to methods for producing a polypeptide comprising using a signal peptide foreign to the polypeptide, nucleic acid constructs comprising a first and a second nucleotide sequence encoding the signal peptide and the polypeptide and expression vectors and host cells comprising said nucleic acid construct.

BACKGROUND OF THE INVENTION

The recombinant production of a heterologous protein in a bacterial host cell, particularly a Gram-positive bacterial cell, such as, *Bacillus*, may provide for a more desirable vehicle for producing the protein in commercially relevant quantities.

Recombinant production of a heterologous protein is generally accomplished by constructing an expression cassette in which the DNA coding for the protein is placed under the expression control of a promoter from a regulated gene, suitable for the host cell. The expression cassette is introduced into the genome of the host cell in one or more copies. Production of the heterologous protein is then achieved by culturing the transformed host cell under inducing conditions necessary for the proper functioning of the promoter contained on the expression cassette.

Improvement of the recombinant production of proteins generally requires the availability of new regulatory sequences which are suitable for controlling the expression of the proteins in a host cell. It is an object of the present invention to provide improved methods for producing a polypeptide in a Gram-positive host cell using signal peptide sequences.

SUMMARY OF THE INVENTION

In a first aspect, the invention provides a method for producing a secreted polypeptide, comprising:
(a) cultivating a Gram-positive host cell in a medium conducive for the production of the polypeptide, wherein the host cell comprises a nucleic acid construct comprising a first nucleotide sequence encoding a signal peptide operably linked to a second nucleotide sequence encoding the polypeptide, wherein the first nucleotide sequence is foreign to the second nucleotide sequence, the 3' end of the first nucleotide sequence is immediately upstream of the second nucleotide sequence, and the first nucleotide sequence is selected from the group consisting of:
(i) a nucleotide sequence encoding a signal peptide having an amino acid sequence which has at least 80% identity with SEQ ID NO:1; or preferably at least 85%, at least 90%, at least 91%, at least 92%, at least 93%, at least 94%, at least 95%, at least 96%, at least 97%, at least 98%, at least 99% or at least 100% identity with SEQ ID NO:1;
(ii) a nucleotide sequence having at least 80% identity with the sequence shown in positions 575 to 661 of SEQ ID NO: 10; or preferably at least 85%, at least 90%, at least 91%, at least 92%, at least 93%, at least 94%, at least 95%, at least 96%, at least 97%, at least 98%, at least 99% or 100% identity with the sequence shown in positions 575 to 661 of SEQ ID NO: 10; and
(iii) a nucleotide sequence which hybridizes under stringency conditions with a polynucleotide having the nucleotide sequence shown in positions 575-661 of SEQ ID NO: 10, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm; and optionally
(b) isolating the secreted polypeptide from the cultivation medium.

In a second aspect, the invention provides a nucleic acid construct comprising a first nucleotide sequence encoding a signal peptide operably linked to a second nucleotide sequence encoding a polypeptide, wherein the first nucleotide sequence is foreign to the second nucleotide sequence, and the 3' end of the first nucleotide sequence is immediately upstream of the second nucleotide sequence, and the first nucleotide sequence is selected from the group consisting of:
(i) a nucleotide sequence encoding a signal peptide having an amino acid sequence which has at least 80% identity with SEQ ID NO:1; or preferably at least 85%, at least 90%, at least 91%, at least 92%, at least 93%, at least 94%, at least 95%, at least 96%, at least 97%, at least 98%, at least 99% or at least 100% identity with SEQ ID NO:1;
(ii) a nucleotide sequence having at least 80% identity with the sequence shown in positions 575 to 661 of SEQ ID NO: 10; or preferably at least 85%, at least 90%, at least 91%, at least 92%, at least 93%, at least 94%, at least 95%, at least 96%, at least 97%, at least 98%, at least 99% or 100% identity with the sequence shown in positions 575 to 661 of SEQ ID NO: 10; and
(iii) a nucleotide sequence which hybridizes under stringency conditions with a polynucleotide having the nucleotide sequence shown in positions 575-661 of SEQ ID NO: 10, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm.

In a third aspect, the invention provides a recombinant expression vector comprising the nucleic acid construct of the second aspect.

The fourth aspect of the invention relates to a recombinant host cell comprising the nucleic acid construct of the second aspect or the expression vector of the third aspect.

In a fifth aspect, the invention relates to the use of a signal peptide for producing a polypeptide in a Gram-positive host cell, wherein the signal peptide is encoded by a first nucleotide sequence and the polypeptide is encoded by a second nucleotide sequence foreign to the first nucleotide sequence, and the 3' end of the first nucleotide sequence is immediately upstream of the second nucleotide sequence, and wherein the first nucleotide sequence is selected from the group consisting of:

(i) a nucleotide sequence encoding a signal peptide having an amino acid sequence which has at least 80% identity with SEQ ID NO:1; or preferably at least 85%, at least 90%, at least 91%, at least 92%, at least 93%, at least 94%, at least 95%, at least 96%, at least 97%, at least 98%, at least 99% or at least 100% identity with SEQ ID NO:1;

(ii) a nucleotide sequence having at least 80% identity with the sequence shown in positions 575 to 661 of SEQ ID NO: 10; or preferably at least 85%, at least 90%, at least 91%, at least 92%, at least 93%, at least 94%, at least 95%, at least 96%, at least 97%, at least 98%, at least 99% or 100% identity with the sequence shown in positions 575 to 661 of SEQ ID NO: 10; and (iii) a nucleotide sequence which hybridizes under stringency conditions with a polynucleotide having the nucleotide sequence shown in positions 575-661 of SEQ ID NO: 10, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm.

DEFINITIONS

Figure 1:
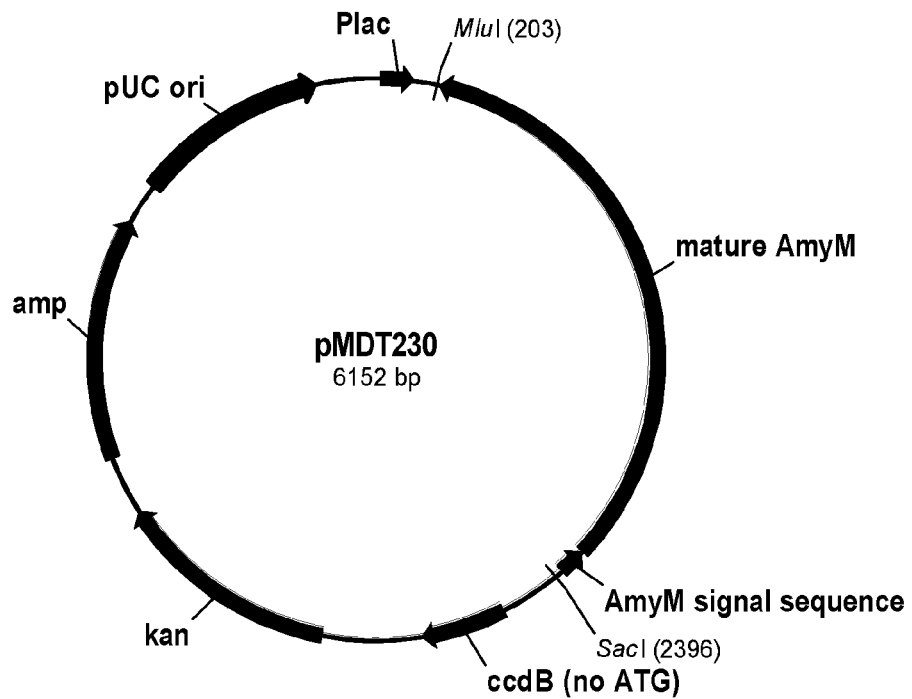
FIG. 1 shows plasmid pMDT230 from Example 1.
Figure 2:
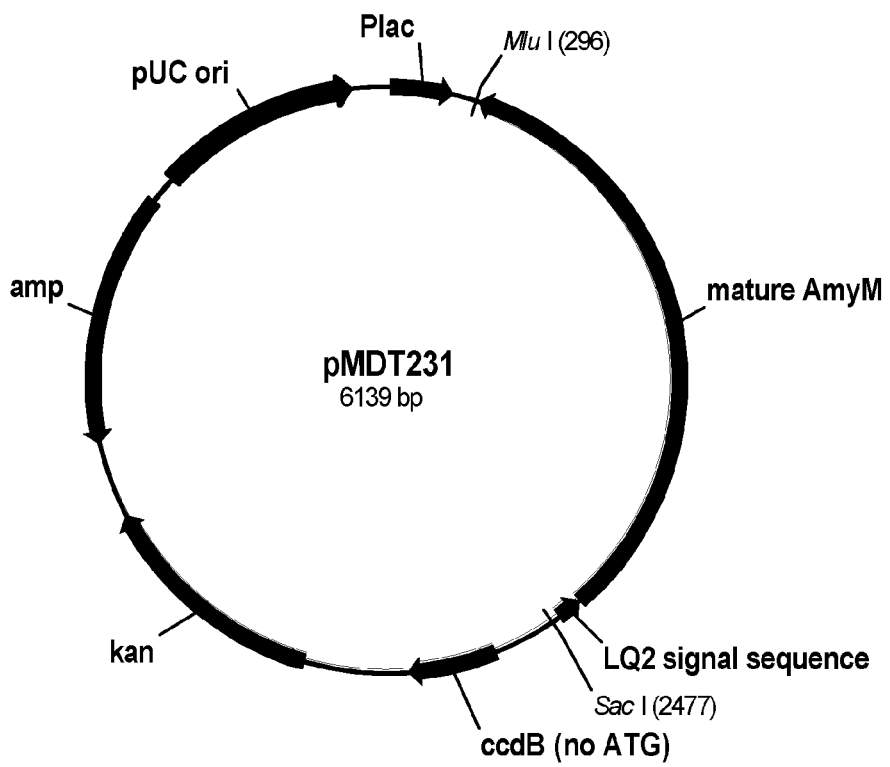
FIG. 2 shows plasmid pMDT231 from Example 1.
Figure 3:
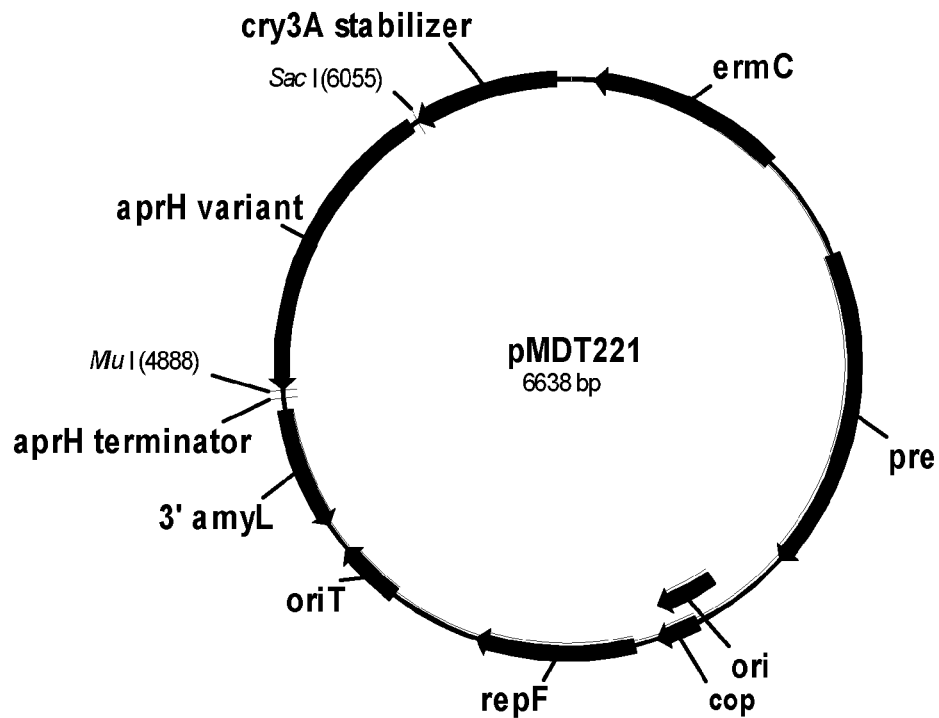
FIG. 3 shows plasmid pMDT221 from Example 1.
Figure 4:
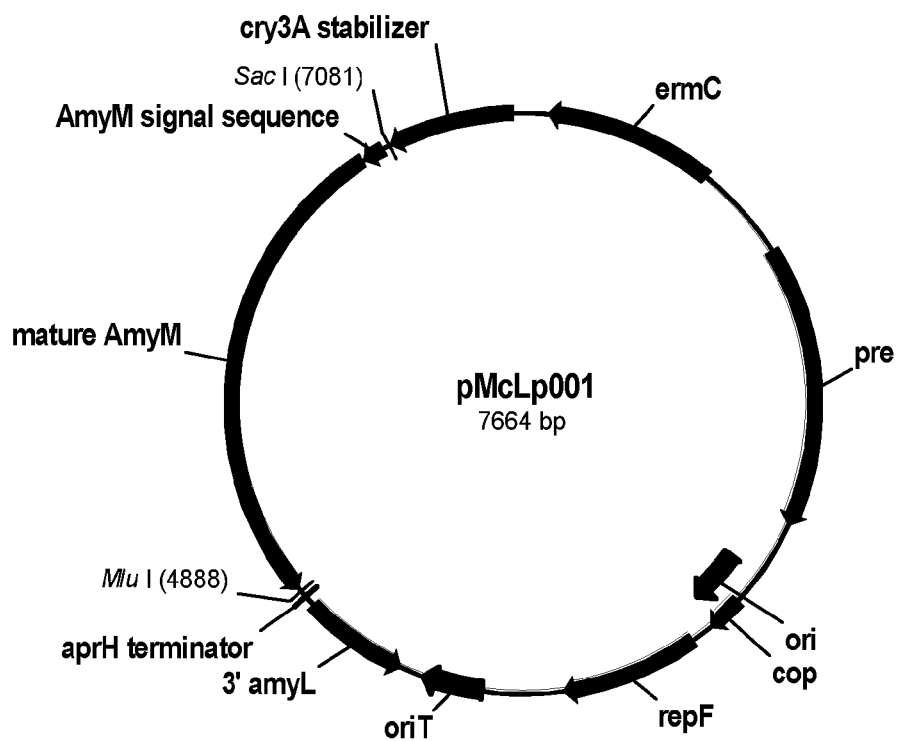
FIG. 4 shows plasmid pMcLp001 from Example 1.
Figure 5:
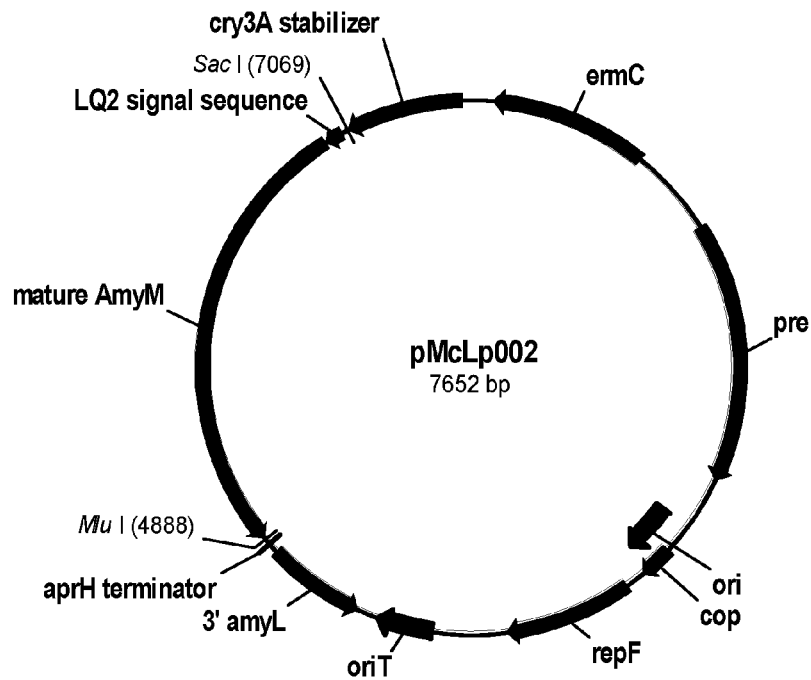
FIG. 5 shows plasmid pMcLp002 from Example 1.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids deleted from the amino and/or carboxyl terminus of a mature polypeptide; wherein the fragment is sweet tasting.

PrsA protein: The PrsA protein of the secretion machinery of *B. subtilis* was disclosed in Kontinen, V. P. and Sarvas, M. (1988, J. Gen. Microbiol., 134:2333-2344) and Kontinen, V. P., et al. (1991, Mol. Microbiol. 5:1273 1283) as well as in WO 94/019471 (Novozymes A/S). The prsA gene, which encodes the PrsA protein, was initially defined by nonlethal mutations that decreased the secretion of several exoproteins (Kontinen, V. P. and Sarvas, M., (1988) J. Gen. Microbiol., 134:2333-2344). Based on the DNA sequence of the cloned prsA gene and subsequent work with this gene and protein, it was asserted that prsA encodes a protein (PrsA) that acts as a chaperone, and is translocated across the cytoplasmic membrane. The PrsA protein has been found to possess a limited amount of sequence homology (about 30%) with the PrtM protein of *Lactococcus* lactis, a protein proposed to assist the maturation of an exported serine protease (Haandrikman, A. J., et al, (1989) J. Bacteriol., 171:2789-2794; Vos, P., et al., (1989) J. Bacteriol., 171:2795 2802).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Isolated or purified: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs the expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the —nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides deleted from the 5' and/or 3' end of a mature polypeptide coding sequence; wherein the subsequence encodes a fragment.

Variant: The term "variant" means a polypeptide comprising an alteration, i.e., a substitution, insertion, and/or deletion of one or more (e.g., several) amino acid residues at one or more positions. A substitution means a replacement of the amino acid occupying a position with a different amino acid; a deletion means removal of the amino acid occupying a position; and an insertion means adding an amino acid adjacent to the amino acid occupying a position.

DETAILED DESCRIPTION OF THE INVENTION

In a first aspect, the invention provides a method for producing a secreted polypeptide, comprising:
(a) cultivating a Gram-positive host cell in a medium conducive for the production of the polypeptide, wherein the host cell comprises a nucleic acid construct comprising a first nucleotide sequence encoding a signal peptide operably linked to a second nucleotide sequence encoding the polypeptide, wherein the first nucleotide sequence is foreign to the second nucleotide sequence, the 3' end of the first nucleotide sequence is immediately upstream of the second nucleotide sequence, and the first nucleotide sequence is selected from the group consisting of:

(i) a nucleotide sequence encoding a signal peptide having an amino acid sequence which has at least 80% identity with SEQ ID NO:1; or preferably at least 85%, at least 90%, at least 91%, at least 92%, at least 93%, at least 94%, at least 95%, at least 96%, at least 97%, at least 98%, at least 99% or at least 100% identity with SEQ ID NO:1;

(ii) a nucleotide sequence having at least 80% identity with the sequence shown in positions 575 to 661 of SEQ ID NO: 10; or preferably at least 85%, at least 90%, at least 91%, at least 92%, at least 93%, at least 94%, at least 95%, at least 96%, at least 97%, at least 98%, at least 99% or 100% identity with the sequence shown in positions 575 to 661 of SEQ ID NO: 10; and (iii) a nucleotide sequence which hybridizes under stringency conditions with a polynucleotide having the nucleotide sequence shown in positions 575-661 of SEQ ID NO: 10, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm; and optionally (b) isolating the secreted polypeptide from the cultivation medium.

The LQ2 signal peptide is a hybrid between the signal peptide of the alpha-amylase from *Bacillus licheniformis* and the signal peptide of the alpha-amylase from *Bacillus amyloliquefaciens*. Amino acids 1-11 of the LQ2 signal peptide are identical to amino acids 1-11 of the *B. licheniformis* alpha-amylase signal peptide, and amino acids 12-28 of the LQ signal peptide are identical to amino acids 20 to 36 of the *B. amyloliquefaciens* alpha-amylase signal peptide. The amino acid sequence of the LQ2 signal peptide is:

```
                                          (SEQ ID NO: 1)
MKQQKRLYARLVLMCTLLFVSLPITKTS
```

In preferred embodiments of the aspects of the invention, the first nucleotide sequence encodes a signal peptide comprising the amino acid sequence of SEQ ID NO: 1; preferably, the first nucleotide sequence encodes a signal peptide consisting of the amino acid sequence of SEQ ID NO: 1, or a peptide fragment thereof that retains the ability to direct the polypeptide into or across a cell membrane, e.g. into the cell's secretory pathway. Even more preferably, the first nucleotide sequence consists of positions 575-661 of SEQ ID NO: 10, or a subsequence thereof which encodes a signal peptide that retains the ability to direct the polypeptide into or across a cell membrane, e.g. into a cell's secretory pathway.

In another embodiment, the first nucleotide sequence encodes a variant signal peptide comprising a substitution, deletion, and/or insertion at one or more (e.g., several) positions. In an embodiment, the number of amino acid substitutions, deletions and/or insertions introduced into the signal peptide of SEQ ID NO:1 is up to 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-5 amino acids; small amino- or carboxyl-terminal extensions.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the signal peptide or change the pH optimum.

Essential amino acids in a signal peptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for signal peptide activity to identify amino acid residues that are critical to the activity of the molecule. See also, Hilton et al., 1996, *J. Biol. Chem.* 271: 4699-4708. The identity of essential amino acids can also be inferred from an alignment with a related signal peptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci.* USA 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The signal peptide may be a hybrid in which a region of one signal peptide is fused at the N-terminus or the C-terminus of a region of another signal peptide.

Sources of Signal Peptides

A signal peptide having of the present invention may be obtained from microorganisms of any genus. For purposes of the present invention, the term "obtained from" as used herein in connection with a given source shall mean that the signal peptide encoded by a polynucleotide is produced by the source or by a strain in which the polynucleotide from the source has been inserted. The signal peptide may be a bacterial signal peptide. For example, the signal peptide may be a Gram-positive bacterial signal peptide such as a *Bacillus, Clostridium, Enterococcus, Geobacillus, Lactobacillus, Lactococcus, Oceanobacillus, Staphylococcus, Streptococcus*, or *Streptomyces* signal peptide.

In one aspect, the signal peptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* signal peptide.

In another aspect, the signal peptide is a *Streptococcus equisimilis, Streptococcus pyogenes, Streptococcus uberis*, or *Streptococcus equi* subsp. *Zooepidemicus* signal peptide.

In another aspect, the signal peptide is a *Streptomyces achromogenes, Streptomyces avermitilis, Streptomyces coelicolor, Streptomyces griseus*, or *Streptomyces lividans* signal peptide.

In a preferred embodiment, the second nucleotide sequence of the invention encodes a polypeptide native or heterologous to the host cell.

Preferably, the second nucleotide sequence of the invention encodes a hormone or hormone variant, enzyme, receptor or portion thereof, antibody or portion thereof, allergen or reporter; and preferably, the enzyme is an oxidoreductase, transferase, hydrolase, lyase, isomerase, or ligase; and most preferably, the enzyme is an aminopeptidase, amylase, carbohydrase, carboxypeptidase, catalase, cellulase, cellobiohydrolase, chitinase, cutinase, cyclodextrin glycosyltransferase, deoxyribonuclease, endoglucanase, esterase, alphagalactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase or beta-xylosidase.

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci.* USA 98: 6289-6294). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

Nucleic Acid Constructs

The present invention also relates to nucleic acid constructs comprising a polynucleotide of the present invention.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci.* USA 75: 3727-3731), as well as the tac promoter (DeBoer et al., 1983, *Proc. Natl. Acad. Sci.*

USA 80: 21-25). Further promoters are described in "Useful proteins from recombinant bacteria" in Gilbert et al., 1980, *Scientific American* 242: 74-94; and in Sambrook et al., 1989, Molecular Cloning: A Laboratory Manual. Examples of tandem promoters are disclosed in WO 99/43835.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus* clausii alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. Other examples of regulatory sequences are those that allow for gene amplification.

The second aspect of the invention relates to a nucleic acid construct comprising a first nucleotide sequence encoding a signal peptide operably linked to a second nucleotide sequence encoding a polypeptide, wherein the first nucleotide sequence is foreign to the second nucleotide sequence, and the 3' end of the first nucleotide sequence is immediately upstream of the second nucleotide sequence, and the first nucleotide sequence is selected from the group consisting of:

(i) a nucleotide sequence encoding a signal peptide having an amino acid sequence which has at least 80% identity with SEQ ID NO:1; or preferably at least 85%, at least 90%, at least 91%, at least 92%, at least 93%, at least 94%, at least 95%, at least 96%, at least 97%, at least 98%, at least 99% or at least 100% identity with SEQ ID NO:1;

(ii) a nucleotide sequence having at least 80% identity with the sequence shown in positions 575 to 661 of SEQ ID NO: 10; or preferably at least 85%, at least 90%, at least 91%, at least 92%, at least 93%, at least 94%, at least 95%, at least 96%, at least 97%, at least 98%, at least 99% or 100% identity with the sequence shown in positions 575 to 661 of SEQ ID NO: 10; and (iii) a nucleotide sequence which hybridizes under stringency conditions with a polynucleotide having the nucleotide sequence shown in positions 575-661 of SEQ ID NO: 10, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm.

In a preferred embodiment of the nucleic acid construct according to the second aspect, the first nucleotide sequence encodes a signal peptide comprising the amino acid sequence of SEQ ID NO: 1; preferably the first nucleotide sequence encodes a signal peptide consisting of the amino acid sequence of SEQ ID NO: 1, or a peptide fragment thereof that retains the ability to direct the polypeptide into or across a cell membrane, e.g. into a cell's secretory pathway; more preferably, the first nucleotide sequence consists of positions 575-661 of SEQ ID NO: 10 or a subsequence thereof, which encodes a signal peptide that retains the ability to direct the polypeptide into or across a cell membrane, e.g. into a cell's secretory pathway.

Expression Vectors

The present invention also relates to recombinant expression vectors comprising a polynucleotide encoding a signal peptide of the present invention operably linked with a promoter, a coding sequence and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Methods of Production

The present invention also relates to methods of producing a polypeptide, comprising (a) cultivating a cell, which produces the polypeptide, under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

EXAMPLES

Example 1

Maltogenic Amylase with LQ2 Signal Peptide

Media

LB medium was composed per liter of 10 g of tryptone, 5 g of yeast extract, and 5 g of NaCl. LB plates were composed of LB medium and 15 g of bacto agar per liter. LB milk plates were composed of LB medium, 10 g of nonfat dry milk per liter, and 15 g of bacto agar per liter. LB milk plates were composed of LB medium, 5 g of starch azure (Sigma-Aldrich, St. Louis, Mo., USA) per liter, and 15 g of bacto agar per liter. LB agar and 5 g starch azure per liter.

2xYT medium was composed per liter of 16 g of Tryptone, 10 g of yeast extract, and 5 g of NaCl. 2xYT ampicillin medium was composed of 2X YT medium and 100 µg of ampicillin per ml. 2xYT ampicillin plates were composed per liter of 2X YT ampicillin medium and 15 g of bacto agar.

TBAB medium was composed of Difco Tryptose Blood Agar Base (BD Diagnostics, Franklin Lakes, N.J., USA).

TBAB erythromycin/lincomycin plates were composed of TBAB medium and 1 μg of erythromycin and 25 μg of lincomycin per ml.

SM1 medium was composed per liter of 6 g (NH$_4$)$_2$HPO$_4$, 26 g J6 Protamyl hydrolysate, 1.2 g MgSO$_4$.7H$_2$O, 36 g KH$_2$PO$_4$, 4.3 g Na$_2$HPO$_4$, 1.8 g K$_2$SO$_4$, 0.1 g CaCl$_2$.2H$_2$O, 28.5 g sucrose, 18 ml MicroPM Low trace metals solution, and 0.5 g SB2121 antifoam, adjusted to pH 7.0.

MicroPM Low trace metals solution was composed per liter of 0.49 g MnSO$_4$.H$_2$O, 1.97 g FeSO$_4$.7H$_2$O, 0.1 g CuSO$_4$.5H$_2$O, 0.3 g ZnCl$_2$, and 19.6 g citric acid.

J6 Protamyl hydrolysate was prepared as follows: 750 g of Avebe Protamyl were added to 8 l of warm water in a 15 l jacketed glass reactor. The solution was sparged with 1 l/min of air through the harvest tube for 5 min and stirred at 500 rpm while heating with a circulating water bath until the temperature reached 55° C. 73 g of Alcalase 2.4 concentrate were diluted in approximately 1 l of water, and the mixture was added to the jacketed glass reactor. Temperature was maintained at 55° C., and pH was maintained at 7.0 using 4 N NaOH. pH control and stirring were stopped 4 h after Alcalase addition, and the volume was adjusted to 10 l with water.

Strains

Bacillus plasmids were constructed in Bacillus subtilis 168Δ4. Bacillus subtilis 168Δ4 was derived from the Bacillus subtilis type strain 168 (BGSC 1A1, Bacillus Genetic Stock Center, Columbus, Ohio) and has deletions in the spoIIAC, aprE, nprE, and amyE genes. The deletion of these four genes was performed essentially as described for Bacillus subtilis A164Δ5, which is described in detail in U.S. Pat. No. 5,891,701.

Conjugal transfer of plasmids from Bacillus subtilis to Bacillus licheniformis recipient strains were performed using conjugation donor host strain Bacillus subtilis AEB711 (disclosed in WO 2008/067423). This strain has a deletion in the alr (dal) gene encoding D-alanine racemase and contains plasmids pBC16 (conferring tetracycline resistance) and pLS20, which confer the ability to mobilize oriT-containing plasmids. The strain further has a gene encoding B. licheniformis DNA methyltransferase M.Bli1904II (WO 2008/067423) inserted in the chromosome at the amyE locus.

The LQ2 Signal Peptide

The LQ2 signal peptide is a hybrid between the signal peptide of the alpha-amylase from Bacillus licheniformis and the signal peptide of the alpha-amylase from Bacillus amyloliquefaciens. Amino acids 1-11 of the LQ2 signal peptide are identical to amino acids 1-11 of the Termamyl signal peptide, and amino acids 12-28 of the LQ signal peptide are identical to amino acids 20 to 36 of the alpha-amylase signal peptide from Bacillus amyloliquefaciens. The amino acid sequence of the LQ2 signal peptide is:

MKQQKRLYARLVLMCTLLFVSLPITKTS (SEQ ID NO:1)

Cloning of Gene Encoding AmyM with Native Signal Peptide

A DNA sequence comprising the amyL ribosome binding site followed by a DNA sequence encoding the native signal peptide and mature peptide of maltogenic alpha-amylase AmyM (NOVAMYL®) was cloned by PCR. Genomic DNA was isolated from Bacillus sp. TS25 according to the procedure of Pitcher et al., 1989, Lett. Appl. Microbiol. 8: 151-156. The amyM coding region was amplified by PCR from TS25 genomic DNA using primers 067827 and 067828 below. The PCR was performed using Phusion® Hot Start DNA Polymerase (New England Biolabs, Inc., Beverly, Mass., USA) according to manufacturer's instructions in a PTC-200 Peltier thermal cycler (MJ Research, Inc., Waltham, Mass., USA) using the following temperature profile:

1 cycle of 96° C. for 2 min;
11 cycles of 94° C. for 30 s; 60° C. for 45 s, decreasing by 1° C. per cycle; and 72° C. for 1 min;
20 cycles of 94° C. for 30 s; 50° C. for 45 s; and 72° C. for 1 min, increasing by 20 s per cycle;
1 cycle of 72° C. for 5 min.

Primer 067827 (SEQ ID NO: 2):
5'-gagctccacattgaaaggggaggagaatcatgaaaaagaaaacgctt Primer 067828 (SEQ ID NO: 3):
5'-acgcgtctagttttgccacgtaac The PCR product was purified using a QIAQUICK® Gel Extraction Kit (QIAGEN Inc., Valencia, Calif., USA) according to the manufacturer's instructions. The purified PCR product was then cloned into vector pCR4Blunt using a Zero Blunt® TOPO® Cloning Kit for Sequencing (Invitrogen, Carlsbad, Calif., USA) and transformed into One Shot® TOP10 Chemically Competent E. coli cells (Invitrogen, Carlsbad, Calif., USA) according to the manufacturer's instructions, selecting for ampicillin resistance on 2xYT ampicillin plates at 37° C. Plasmid DNA was isolated from one transformant using a QIAGEN Plasmid Midi Kit (QIAGEN Inc., Valencia, Calif., USA) and the correct sequence was confirmed by DNA sequencing. This plasmid was designated pMDT230.

Construction of LQ2-AmyM Gene Fusion

A DNA sequence encoding a fusion of the LQ2 signal peptide and mature AmyM polypeptide was constructed by PCR using splicing by overlap extension (SOE). Bacillus subtilis BW229 is a derivative of Bacillus subtilis A164 with the amyL ribosome binding site and LQ2 signal peptide coding sequence integrated in the chromosome at the amyE locus (disclosed in WO 2011/084695). Genomic DNA was isolated from BW229 according to the procedure of Pitcher et al., 1989, supra. The amyL ribosome binding site and LQ2 signal peptide coding sequence were amplified by PCR from BW229 genomic DNA using primers 998291 and 067830 below. The PCR was performed using Phusion® Hot Start DNA Polymerase (New England Biolabs, Inc., Beverly, Mass., USA) according to manufacturer's instructions in a RoboCycler Gradient 40 thermal cycler (Stratagene Corporation, La Jolla, Calif., USA) using the following temperature profile:

1 cycle of 30 s at 98° C.;
30 cycles of 30 s at 98° C., 30 s at 55° C., and 30 s at 72° C.

Primer 998291 (SEQ ID NO: 4):
5'-gagctccacattgaaaggggaggagaa

Primer 067830 (SEQ ID NO: 5):
5'-ggaactgctggctgatgttttttgtaatc

The coding region of mature AmyM was amplified by PCR from Bacillus sp. TS25 genomic DNA using primers 067829 and 067828 below. The PCR was performed using Phusion® Hot Start DNA Polymerase (New England Biolabs, Inc., Beverly, Mass., USA) according to manufacturer's instructions in a PTC-200 Peltier thermal cycler (MJ Research, Inc., Waltham, Mass., USA) using the following temperature profile:

1 cycle of 96° C. for 2 min;
11 cycles of 94° C. for 30 s; 60° C. for 45 s, decreasing by 1° C. per cycle; and 72° C. for 1 min;
20 cycles of 94° C. for 30 s; 50° C. for 45 s; and 72° C. for 1 min, increasing by 20 s per cycle;
1 cycle of 72° C. for 5 min.

Primer 067829 (SEQ ID NO: 6):
5'-acatcagccagcagttccgcaagcgtca

Primer 067828 (SEQ ID NO: 7):
5'-acgcgtctagtttttgccacgtaac

The PCR products were purified using a QIAQUICK® Gel Extraction Kit according to the manufacturer's instructions. The purified PCR products were then fused into a single PCR product by SOE PCR using primers 998291 and 067828. The PCR was performed using Phusion® Hot Start DNA Polymerase (New England Biolabs, Inc., Beverly, Mass., USA) according to manufacturer's instructions in a RoboCycler Gradient 40 thermal cycler (Stratagene Corporation, La Jolla, Calif., USA) using the following temperature profile:
1 cycle of 30 s at 98° C.;
30 cycles of 30 s at 98° C., 30 s at 55° C., and 30 s at 72° C.

The resulting PCR product comprised the amyL ribosome binding site followed by a DNA sequence encoding a fusion of LQ2 signal peptide and mature AmyM. The PCR product was purified using a QIAQUICK® Gel Extraction Kit according to the manufacturer's instructions. The purified PCR product was then cloned into vector pCR4Blunt using a Zero Blunt® TOPO® Cloning Kit for Sequencing and transformed into One Shot® TOP10 Chemically Competent *E. coli* cells according to the manufacturer's instructions, selecting for ampicillin resistance on 2XYT ampicillin plates at 37° C. Plasmid DNA was isolated from one transformant using a QIAGEN Plasmid Midi Kit (QIAGEN Inc., Valencia, Calif., USA) and the sequence was confirmed by DNA sequencing. This plasmid was designated pMDT231.

Construction of Plasmids for Insertion of amyM Expression Cassettes at *Bacillus licheniformis* amyL Locus Plasmid pMDT221 was used as a vector for insertion of the amyM gene at the amyL locus of *Bacillus licheniformis*. Plasmid pMDT221 is based on temperature-sensitive plasmid pE194 (Horinouchi and Weisblum, 1982, *J. Bacteriol*. 150: 804-814) and comprises the erythromycin-resistance marker ermC, replication factor repF, and origin of replication of pE194. It further comprises the oriT region of plasmid pUB110 (McKenzie et al., 1986, Plasmid, 15: 93-103), rendering it mobilizable by conjugation. It also comprises a region from the 5' untranslated region of the cry3A gene of *Bacillus thuringiensis* subsp. *tenebrionis* (Agaisse and Lereclus, 1996, *Mol. Microbiol*. 20: 633-643) followed the coding region and transcription terminator of a variant of protease gene aprH (WO 2003/006602) and a fragment of the 3' end of the *Bacillus licheniformis* amyL gene. As such, pMDT221 is similar to plasmid pTH013 (WO 2005/098016), which has essentially the same structure except for the presence of a gene encoding a mannanase in place of the aprH variant.

Plasmid pMcLp001 was constructed by replacement of the aprH variant in pMDT221 with the amyM gene from pMDT230. Plasmid pMDT221 was digested with restriction endonucleases SacI and MluI and analyzed by 0.8% agarose electrophoresis in TBE buffer, and an approximately 5471 bp vector fragment was purified using a QIAQUICK® Gel Extraction Kit. Plasmid pMDT230 was digested with SacI and MluI and analyzed by 0.8% agarose electrophoresis in TBE buffer, and an approximately 2193 bp fragment comprising the amyL RBS and amyM coding sequence was purified using a QIAQUICK® Gel Extraction Kit. The pNBT24 vector fragment and the amyM fragment were ligated together with T4 DNA ligase (New England Biolabs, Inc., Beverly, Mass., USA) according to the manufacturer's instructions, and *Bacillus subtilis* 168Δ4 was transformed with the ligation according to the procedure of Anagnostopoulos and Spizizen, 1961, *J. Bacteriol*. 81: 741-746, selecting for erythromycin resistance on TBAB erythromycin/lincomycin plates at 34° C. Plasmid DNA from one transformant was purified using QIAGEN Plasmid Midi Kit and confirmed by DNA sequencing. This plasmid was designated pMcLp001 and is a temperature-sensitive plasmid bearing the amyL RBS and amyM coding sequence flanked by the cry3A mRNA stabilizer region upstream and the 3' end of the amyL gene downstream.

Plasmid pMcLp002 was constructed by replacement of the aprH variant in pMDT221 with the amyM gene from pMDT231. Plasmid pMDT221 was digested with SacI and MluI and analyzed by 0.8% agarose electrophoresis in TBE buffer, and an approximately 5471 bp vector fragment was purified using a QIAQUICK® Gel Extraction Kit. Plasmid pMDT231 was digested with SacI and MluI and analyzed by 0.8% agarose electrophoresis in TBE buffer, and an approximately 2181 bp fragment comprising the amyL RBS and LQ2-AmyM coding sequence was purified using a QIAQUICK® Gel Extraction Kit. The pNBT24 vector fragment and the amyM fragment were ligated together with T4 DNA ligase (New England Biolabs, Inc., Beverly, Mass., USA) according to the manufacturer's instructions, and *Bacillus subtilis* 168Δ4 was transformed with the ligation according to the procedure of Anagnostopoulos and Spizizen, 1961, supra, selecting for erythromycin resistance on erythromycin resistance on TBAB erythromycin/lincomycin plates at 34° C. Plasmid DNA from one transformant was purified using QIAGEN Plasmid Midi Kit and confirmed by DNA sequencing. This plasmid was designated pMcLp002 and is a temperature-sensitive plasmid bearing the amyL RBS and LQ2-AmyM coding sequence flanked by the cry3A mRNA stabilizer region upstream and the 3' end of the amyL gene downstream.

Construction of *Bacillus licheniformis* amyM Integrants.

Plasmids pMcLp001 and pMcLp002 were introduced into conjugation donor strain *Bacillus subtilis* AEB711 for transfer to *Bacillus licheniformis* by conjugation. *Bacillus subtilis* AEB711 was transformed individually with pMcLp001 according to the procedure of Anagnostopoulos and Spizizen, 1961, supra, selecting for erythromycin resistance on erythromycin resistance on TBAB erythromycin/lincomycin plates at 34° C., and a resulting transformant was designated *Bacillus subtilis* AEB711/pMcLp001. *Bacillus subtilis* AEB711 was transformed individually with pMcLp002 according to the procedure of Anagnostopoulos and Spizizen, 1961, supra, selecting for erythromycin resistance on erythromycin resistance on TBAB erythromycin/lincomycin plates at 34° C., and a resulting transformant was designated *Bacillus subtilis* AEB711/pMcLp002.

*Bacillus subtilis* donor strains AEB711/pMcLp001 and AEB711/pMcLp002 were used to transfer plasmids pMcLp001 and pMcLp002 to *Bacillus licheniformis* recipient strain TH3 (WO 2005/123915) by conjugation. *Bacillus licheniformis* TH3 was grown overnight at 34° C. on LB plates. *Bacillus subtilis* AEB711/pMcLp001 and AEB711/ pMcLp002 were grown overnight at 34° C. on TBAB erythromycin/lincomycin plates supplemented with 100 µg of D-alanine and 10 µg of tetracycline. Cells of each strain were then scraped from the plates and each donor strain was mixed with the recipient strain on a TBAB plate supplemented with 100 µg of D-alanine, forming a circle ~2 cm in diameter.

The plates were incubated at 34° C. for approximately 5 hours. Under these conditions, both the donor and recipient strain were able to grow, and the plasmid could be transferred by conjugation from donor to recipient. Cells were then scraped from the plates, suspended in 1 ml of LB medium, aliquots were spread on TBAB erythromycin/lincomycin plates, and the plates were incubated overnight at 34° C. Under these conditions, only Bacillus licheniformis transconjugants (recipient cells that had received the plasmid by conjugal transfer) were able to grow. The absence of D-alanine prevented growth of the alr-negative donor, and the presence of erythromycin prevented growth of the original recipient.

Plasmids pBC16 and pLS20 may also be transferred from the donor strain by conjugation, so transconjugants were screened for the absence of pBC16 by inability to grow on medium containing tetracycline and for absence of pLS20 by PCR. One erythromycin-resistant transconjugant from the pMcLp001 conjugation that had neither pBC16 nor pLS20 was designated Bacillus licheniformis TH3/pMcLp001, and one erythromycin-resistant transconjugant from the pMcLp002 conjugation that had neither pBC16 nor pLS20 was designated Bacillus licheniformis TH3/pMcLp002.

Bacillus licheniformis TH3 has an expression cassette comprising the $P_{amyL4199}/P_{amyQsc}/P_{cry3A}$/cry3A stabilizer triple tandem promoter (P17) (WO 2005/123915) followed by a gene encoding protease JP170 inserted at the amyL locus of the chromosome. The JP170 subtilase was described as protease A in WO 88/01293 to Novozymes. Later the patent application WO 98/56927 to Novozymes Biotech disclosed the amino acid (polypeptide) sequence of JP170 and the DNA sequence encoding JP170. The amyM genes of plasmids pMcLp001 and pMcLp002 were inserted at the amyL locus of Bacillus licheniformis TH3, replacing the JP170 protease gene, by double homologous recombination. Bacillus licheniformis strains TH3/pMcLp001 and TH3/pMcLp002 were streaked for single colonies on TBAB erythromycin/lincomycin plates at 50° C. in order to select integrants in which the plasmid had inserted by homologous recombination at the amyL locus, via either the cry3A mRNA stabilizer region or the 3' amyL region. Integrants were then grown on LB plates at 34° C. to allow the integrated plasmid to excise from the chromosome. Colonies were then screened for inability to grow on TBAB erythromycin/lincomycin plates at 37° C., indicating loss of the plasmid. Such colonies were further screened for inability to form a zone of clearing on LB milk plates, indicating loss of the JP170 protease gene, and ability to form a zone of clearing on LB starch azure plates, indicating introduction of the amyM gene.

One such integrant resulting from Bacillus licheniformis TH3/pMcLp001 was designated Bacillus licheniformis MCLP15, which has inserted at the amyL locus an expression cassette comprising the triple tandem promoter (P17), the amyL RBS, a coding region encoding the AmyM protein with its native signal peptide, and the amyL transcription terminator.

Another integrant resulting from Bacillus licheniformis TH3/pMcLp002 was designated Bacillus licheniformis MCLP16, which has inserted at the amyL locus an expression cassette comprising the triple tandem promoter (P17), the amyL RBS, a coding region encoding the AmyM protein with the LQ2 signal peptide, and the amyL transcription terminator.

AmyM Expression of Bacillus licheniformis Strains MCLP15 and MCLP16

Shake flask cultures of Bacillus licheniformis MCLP15 and MCLP16 were compared for AmyM production. Bacillus licheniformis MCLP15 and MCLP16 were grown for 5 hours in 3 ml LB broth in Falcon 2059 test tubes at 37° C. with shaking at 250 rpm. For each strain three 125 ml baffled shake flasks containing 25 ml SM1 medium were each inoculated with 0.5 ml of the starter culture and incubated at 37° C. with shaking at 250 rpm. Samples were taken at three and four days of incubation and assayed for maltogenic α-amylase activity. As shown in Table 1 and FIG. 1. AmyM activity in the MCLP16 cultures exceeded that in the MCLP15 cultures by a factor of approximately 3.5-fold after three days and approximately 4.3-fold at four days.

Maltogenic α-amylase activity was determined as follows: This method is used in conjunction with a Beckman Coulter Biomek 3000 and Biomek NX (Beckman Coulter, Inc, Fullerton Calif., USA). Culture broths were diluted appropriately in 0.1 M Na-acetate, 0.01% Triton X-100 buffer pH 5.0 (sample buffer) followed with a series dilution from O-fold to ⅓-fold to ⅑-fold of the diluted sample. AmyL standard was diluted using 2-fold steps starting with a 10 MANU/ml concentration and ending with a 1.25 MANU/ml concentration in the sample buffer. A total of 20 µl of each dilution including standard was transferred to a 96-well flat bottom plate. One hundred micro-liters of a maltotriose substrate solution (20 mg/ml maltotriose, 0.1 M Na-acetate, pH 5.0) was added to each well and then incubated at ambient temperature for 45 min. Upon completion of the incubation the reaction was quenched with 100 µl of 0.06 N NaOH. A total of 20 µl of each of the quenched samples including the standard was transferred to a new 96-well flat bottom plate. Two hundred micro-liters of a Liquid Glucose Oxidase Reagent (Pointe Scientific, Inc, reagent kit 23666-286) were dispensed into the 20 µl of sample. The rate of this reaction was measured at ambient temperature using an optical density of 490 nm for a total of 8 min. Sample concentrations were determined by extrapolation from the generated standard curve.

TABLE 1

Relative AmyL production in shake flask cultures of Bacillus licheniformis MCLP15 and MCLP16.

| Strain | Relative Mean AmyL Titer, Day 3 | Relative Mean AmyL Titer, Day 4 |
|---|---|---|
| MCLP15 | 99.6% | 100.0% |
| MCLP16 | 344.8% | 431.5% |

Example 2

Construction of the Plasmid pAEB802 for Insertion of a Gene Encoding FB024 with the Native Signal Peptide in the Chromosome of B. licheniformis Strains Bacillus plasmids were constructed in Bacillus subtilis 168Δ4. Bacillus subtilis 168Δ4 is derived from the Bacillus subtilis type strain 168 (BGSC 1A1, *Bacillus* Genetic Stock Center, Columbus, Ohio) and has deletions in the spoIIAC, aprE, nprE, and amyE genes. The deletion of these four genes was performed essentially as described for *Bacillus subtilis* A164Δ5, which is described in detail in U.S. Pat. No. 5,891,701.

*B. subtilis* PP289-5: Donor strain for conjugative transfer of plasmids with an origin of transfer, oriT, derived from pUB110 (U.S. Pat. No. 6,066,473).

*B. licheniformis* JA2643: based on SJ1707. A heterologous tandem promoter (as disclosed in WO 1999/043835), followed by a gene (aprJP170) encoding a protease was inserted in the amyL region, leading to a deletion in the amyL gene. A second copy of this tandem triple promoter was inserted in the xylA region, leading to a deletion in the xylA gene. Deletions were also introduced in protease genes aprL, C-component, vpr, bprAB, epr, and wprA, rendering them inactive.

*B. licheniformis* SJ1707: disclosed in WO 93/10249.

*B. licheniformis* AEB847: JA2643 amyL::tandem promoter-fb024, this study

*B. licheniformis* AEB851: JA2643 amyL::tandem promoter-lq2_fb024, this study

Figure 7:
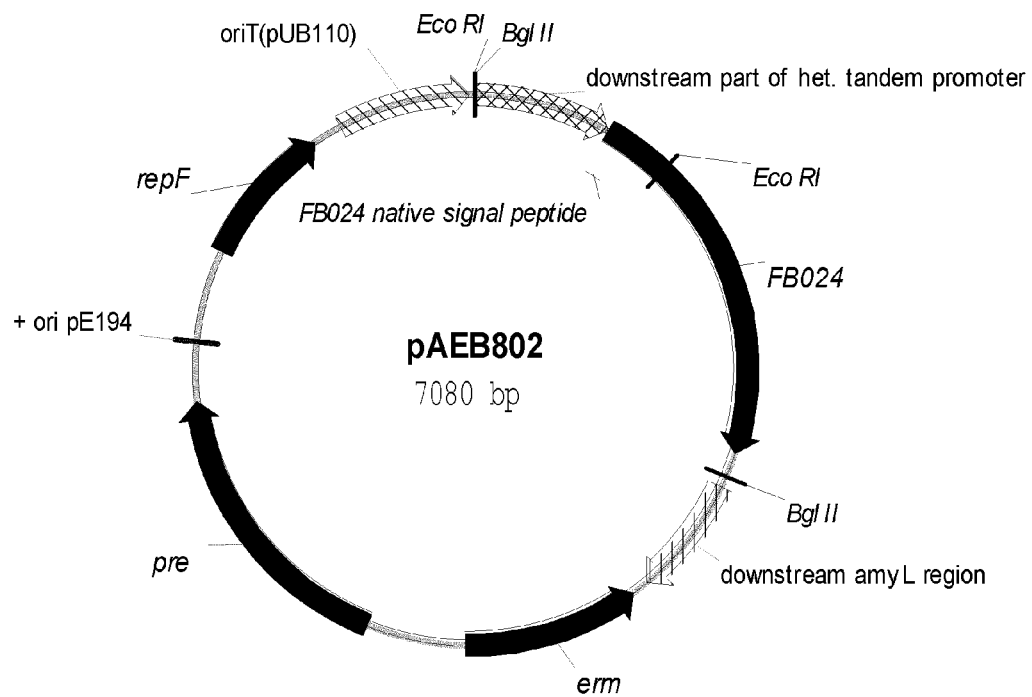
FIG. 7 shows plasmid pAEB802 from Example 2.

Plasmids pSJ6270: Cloning vector for *E. coli* with the ColE1 origin of replication and the bla gene, encoding ampicillin resistance.

pSJ6321: A derivative of pSJ2739 (U.S. Pat. No. 6,100,063). pSJ2739 is derived from pE194, a plasmid with a temperature-sensitive origin of replication capable of directing replication in *Bacillus* strains. pSJ6321 also contains oriT, an origin of transfer from plasmid pUB110.

pAEB802 is pSJ6321 with fb024 surrounded by upstream and downstream regions enabling insertion by double homologous recombination of the fb024 gene downstream of the heterologous tandem promoter in the amyL locus in JA2643. The entire nucleotide sequence of pAEB802 is given in SEQ ID NO:8 and the map is shown in FIG. 7; the encoded FB024 is shown in SEQ ID NO:9.

pAEB909 is pSJ6321 with lq_fb024 surrounded by upstream and downstream regions enabling insertion by double homologous recombination of the fb024 gene downstream of the heterologous tandem promoter in the amyL locus in JA2643. The entire nucleotide sequence of pAEB909 is given in SEQ ID NO:10; the encoded FB024 is shown with the LQ2 signal peptide in SEQ ID NO:11.

Figure 6:
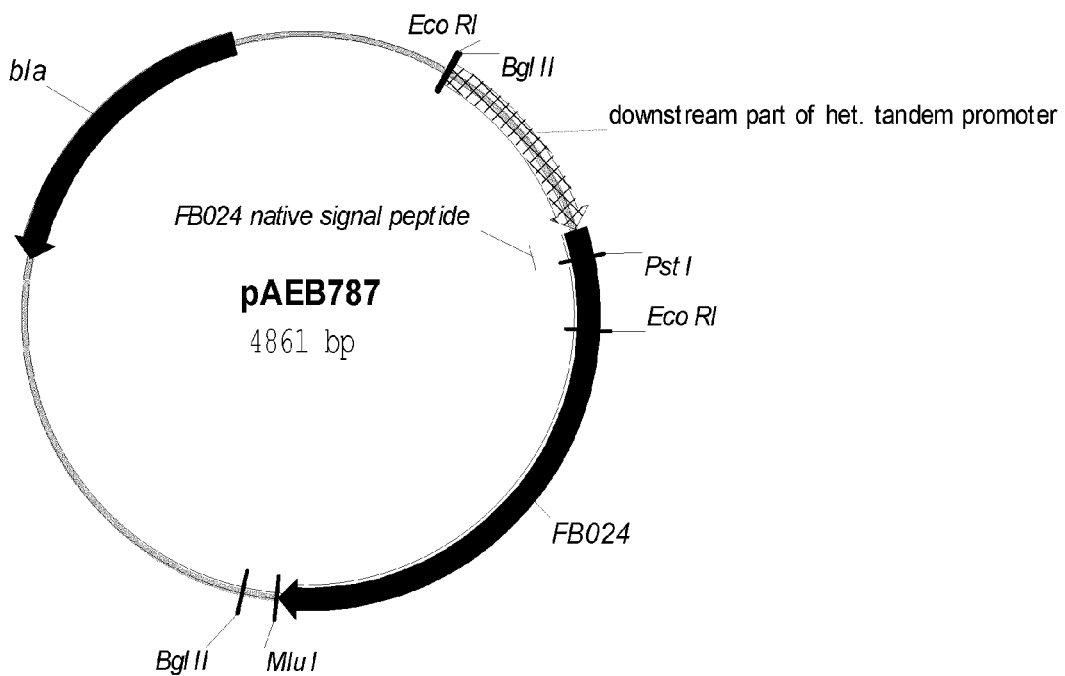
FIG. 6 shows plasmid pAEB787 from Example 2.

The FB024 alpha-amylase with its native signal peptide is encoded by the gene fb024. fb024 was amplified by PCR using TVB281-fwd (a cloning vector with the fb024 gene) as template and the primers pab182 (SEQ ID NO:12) and pab322 (SEQ ID NO:13), resulting in a 1.6 kb PCR fragment. The PCR fragment was digested with PstI and MluI and inserted in the 3.4 kb PstI-MluI fragment of the *E. coli* cloning vector pSJ6270, resulting in plasmid pAEB787. In pAEB787 the downstream part of a heterologous tandem promoter described in WO 1999/043835 is located upstream of fb024. A map of pAEB787 is shown in FIG. 6.

The 2.2 kb Bg/II fragment from pAEB787 was ligated to the 4.9 kb Bg/II fragment from the *B. subtilis* vector pSJ6321, resulting in plasmid pAEB802. In pAEB802 a fragment identical to a region downstream of the amyL gene in *B. licheniformis* is inserted downstream of fb024 cassette. A map of pAEB802 is shown in FIG. 7. The sequence of the entire plasmid is given in SEQ ID NO:8.

Example 3

Construction of the Plasmid pAEB909 for Insertion of a Gene Encoding FB024 with the LQ2 Signal Peptide in the Chromosome of *B. licheniformis*

Figure 8:
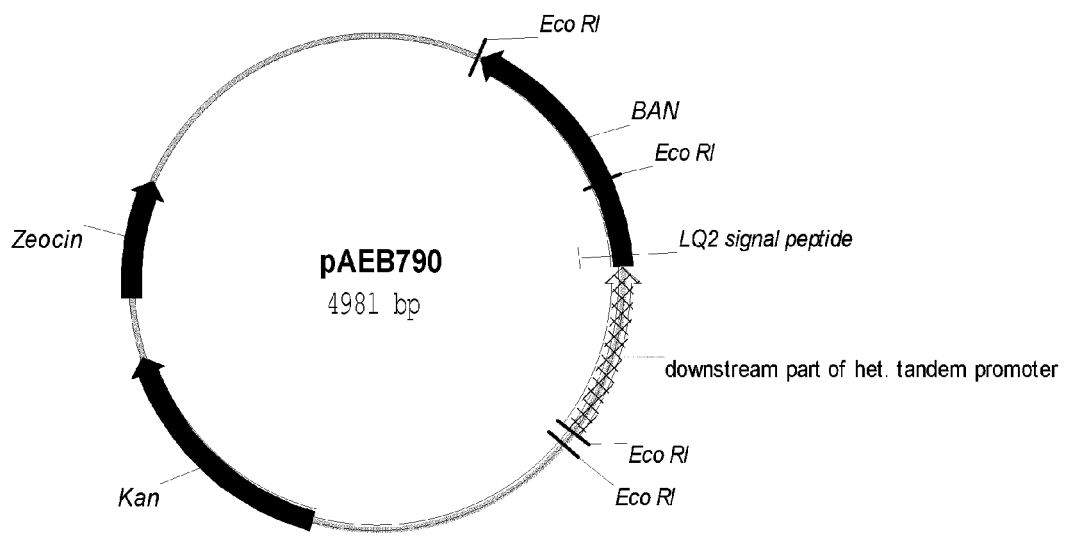
FIG. 8 shows plasmid pAEB790 from Example 3.

The nucleotide sequences of the 5' end of FB024 and *B. amyloliquefaciens* alpha-amylase are identical. Therefore, to replace the native FB024 signal peptide with the LQ2 signal peptide, the upstream part of the FB024 gene and signal peptide was replaced with the corresponding region of the *B. amyloliquefaciens* gene, to which the LQ2 signal peptide had previously been fused. The upstream part of amyQ with the desired features was obtained from plasmid pAEB790, which is an *E. coli* cloning vector with the downstream part of the tandem heterologous promoter, followed by the upstream part of the LQ2_BAN amylase gene. A map of pAEB790 is shown in FIG. 8.

Figure 9:
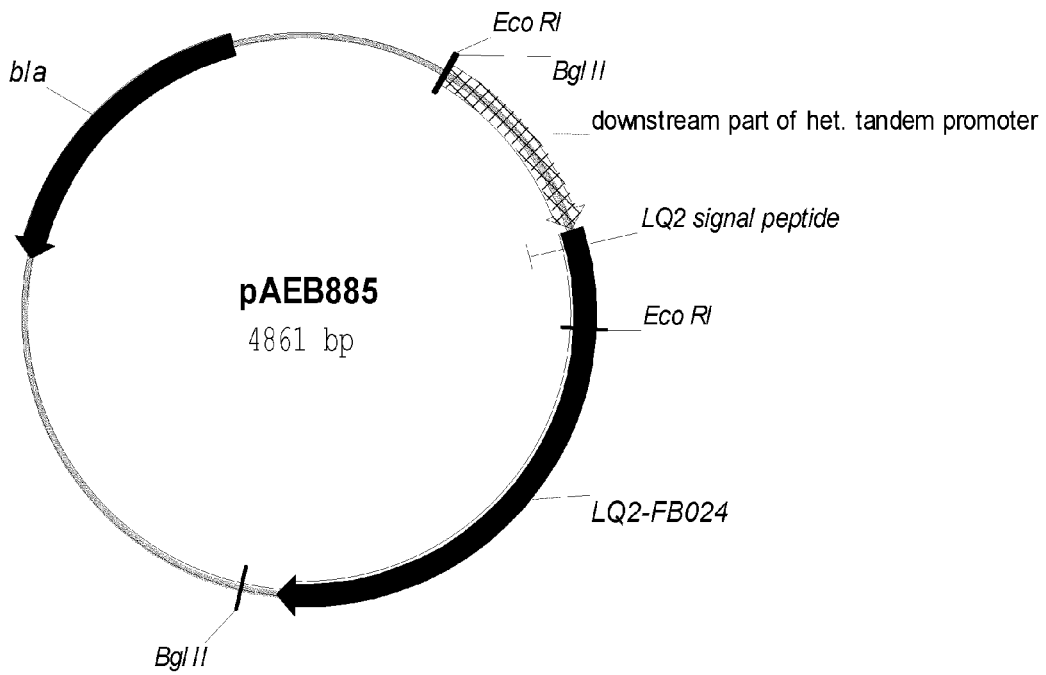
FIG. 9 shows plasmid pAEB885 from Example 3.
Figure 10:
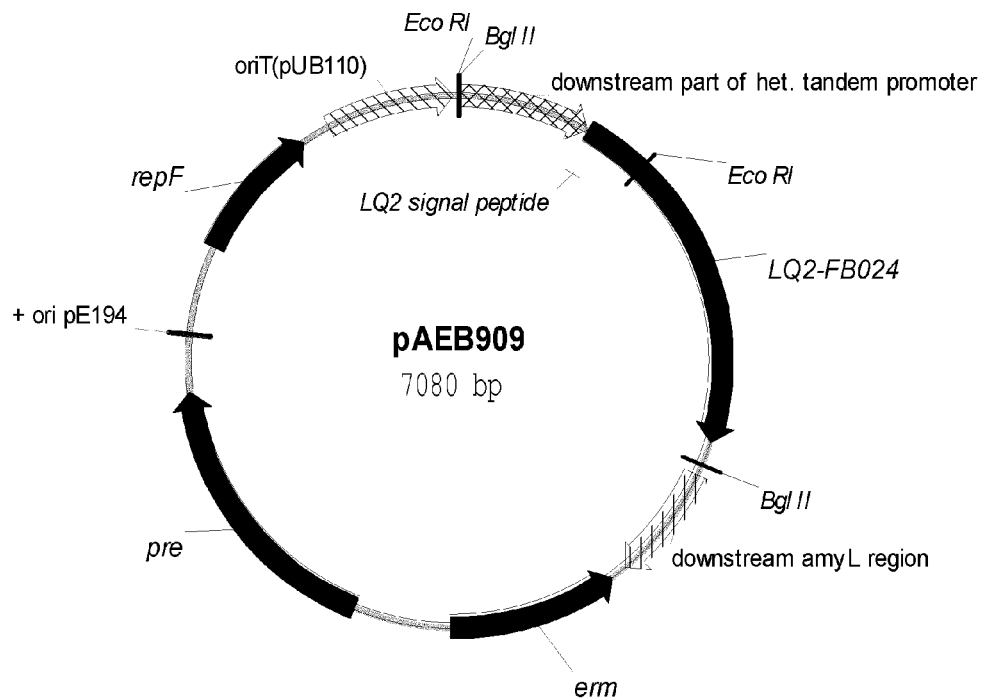
FIG. 10 shows plasmid pAEB909 from Example 3.

The 0.9 kb EcoRI fragment from pAEB790 was joined to the 4.0 kb EcoRI fragment from pAEB787 by ligation, resulting in plasmid pAEB885. The LQ2-FB024 fusion gene on a 2.2 kb Bg/II fragment from pAEB885 was ligated to the 4.9 kb BglII fragment from pSJ6321, resulting in pAEB909. A map of pAEB885 is shown in FIG. 9. A map of pAEB909 is shown in FIG. 10. The entire sequence of pAEB909 is given in SEQ ID NO:10.

Example 4

Insertion of the Gene Encoding FB024 with its Native Signal Peptide or with the LQ2 Signal Peptide in amyL in *B. licheniformis*

Plasmids pAEB802 and pAEB909 were introduced in *B. licheniformis* JA2643 by conjugation using the conjugation donor PP289-5. The fb024 gene was inserted after the heterologous tandem promoter in the amyL locus by double homologous recombination in the regions upstream and downstream of the fb024 gene, placing the gene directly under the control of the promoter. Since a deletion was introduced in amyL in JA2643 it does not produce clearing zones on starch plates. Expressing FB024 renders the strain amylase+, and correct strains could thus be identified as giving rise to clearing zones on starch plates.

When pAEB802 was used in this procedure, a strain was obtained which had the gene encoding FB024 with the native signal peptide inserted after the heterologous tandem promoter in amyL. This strain was named AEB847. The DNA sequence of the *B. licheniformis* amyL region in AEB847 is given in SEQ ID NO:14; the encoded FB024 with its native signal peptide is shown in SEQ ID NO:15.

Figure 11:
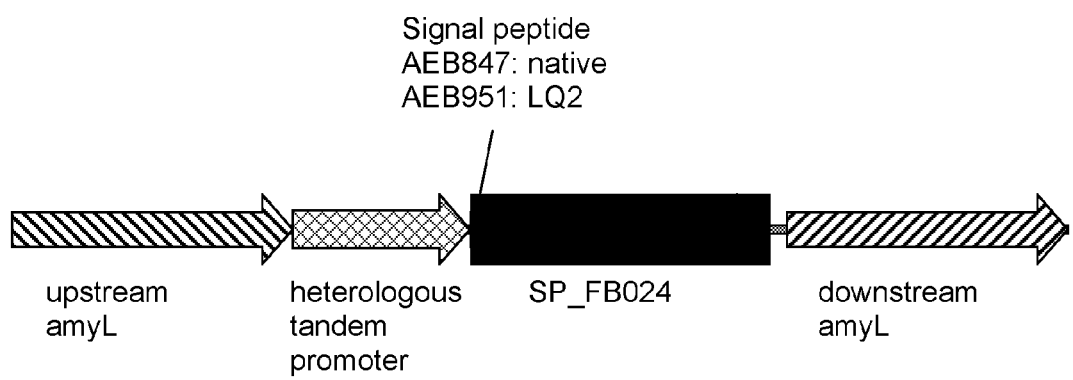
FIG. 11 shows maps of the chromosomal amyL regions of the two strains AEB847 and AEB951 with inserted fragments, from Example 4.

When pAEB909 was used, the strain obtained had the gene encoding FB024 fused to the LQ2 signal peptide inserted in amyL. This strain was named AEB951. The DNA sequence of the *B. licheniformis* amyL region in AEB951 is given in SEQ ID NO:16; the encoded FB024 with the hybrid LQ2 signal peptide is shown in SEQ ID NO:17. Maps of the amyL regions with inserted fragments in AEB847 and AEB951 are given in FIG. 11.

Example 5

Fed Batch Fermentations AEB847 and AEB951 and Resulting FB024 Yields

All media were sterilized by methods known in the art. Unless otherwise described, tap water was used. The ingredient concentrations referred to in the below recipes are before any inoculation. AEB847 and AEB951 were fermented and yields of amylase FB024 were measured.

First Inoculum Medium:

LB agar: 10 g/l peptone from casein; 5 g/l yeast extract; 10 g/l Sodium Chloride; 12 g/l Bacto-agar adjusted to pH 6.8 to 7.2. Premix from Merck was used.

Transfer Buffer:

M-9 buffer (deionized water is used): Di-Sodium hydrogen phosphate, $2H_2O$ 8.8 g/l; Potassium dihydrogen phosphate 3 g/l; Sodium Chloride 4 g/l; Magnesium sulphate, 7H2O 0.2 g/l.

Inoculum Shake Flask Medium:

PRK-50: 110 g/l soy grits; Di-Sodium hydrogen phosphate, $2H_2O$ 5 g/l; pH adjusted to 8.0 with $NaOH/H_3PO_4$ before sterilization.

Make-Up Medium:

Tryptone (Casein hydrolysate from Difco) 30 g/l; Magnesium sulphate, $7H_2O$ 4 g/l; DiPotassium hydrogen phosphate 7 g/l; Di-Sodium hydrogen phosphate, $2H_2O$ 7 g/l; DiAmmonium sulphate 4 g/l; Citric acid 0.78 g/l; Vitamins (Thiamin-dichlorid 34.2 mg/l; Riboflavin 2.9 mg/l; Nicotinic acid 23 mg/l; Calcium D-pantothenate 28.5 mg/l; Pyridoxal-HCl 5.7 mg/l; D-biotin 1.1 mg/l; Folic acid 2.9 mg/l); Trace metals ($MnSO_4$, $H_2O$ 39.2 mg/l; $FeSO_4$, $7H_2O$ 157 mg/l; $CuSO_4$, $5H_2O$ 15.6 mg/l; $ZnCl_2$ 15.6 mg/l); Antifoam (SB2121) 1.25 ml/l; pH adjusted to 6.0 with $NaOH/H_3PO_4$ before sterilization.

Feed Medium:

Sucrose 708 g/l

Procedure for Inoculum Steps:

The strain was grown on LB agar slants 1 day at 37° C. The agar was washed with M-9 buffer. The optical density (OD) at 650 nm of the resulting cell suspension was measured. The inoculum shake flask (PRK-50) was inoculated with an inoculum of OD (650 nm)×ml cell suspension=0.1. The shake flask was incubated at 37° C. at 300 rpm for 20 hr. The fermentation in the main fermentor (fermentation tank) was started by inoculating the main fermentor with the growing culture from the shake flask. The inoculated volume was 11% of the make-up medium (80 ml for 720 ml make-up media).

Fermentor Equipment:

Standard lab fermentors were used equipped with a temperature control system, pH control with ammonia water and phosphoric acid, dissolved oxygen electrode to measure >20% oxygen saturation through the entire fermentation.

Fermentation Parameters:

Temperature: 38° C. The pH was kept between 6.8 and 7.2 using ammonia water and phosphoric acid. Control: 6.8 (ammonia water); 7.2 phosphoric acid. Aeration: 1.5 liter/min Agitation: 1500 rpm.

Feed Strategy:

0 hr: 0.05 g/min/kg initial broth after inoculation. 8 hr: 0.156 g/min/kg initial broth after inoculation. End: 0.156 g/min/kg initial broth after inoculation Experimental Setup:

The fermentations were run for three days. Samples were withdrawn during the fermentations and α-amylase activity was determined by a standard amylase assay based on colorimetric measurements and a PNP-containing (p-nitrophenol) substrate, such as, 4,6-ethylidene($G_7$)-p-nitrophenyl ($G_1$)-α,D-maltoheptaoside, which is converted by α-amylase into, e.g., $G_2$-PNP and $G_3$-PNP, which are in turn degraded by α-glucosidase (added in excess to the reaction) to glucose and the yellow p-nitrophenol to be measured.

Thus, it is clear from table 2 that the strain with LQ2 signal peptide (AEB951) gave approximately 50% higher activity than the strain with the native FB024 signal peptide (AEB851) throughout the fermentation.

TABLE 2

| Day of fermentation | Results (normalized to 100% for the highest activity) | | |
|---|---|---|---|
| | Strains | | Relative activity |
| | AEB847 | AEB951 | AEB951/AEB847 |
| 1 | 35 | 54 | 1.54 |
| 2 | 60 | 88 | 1.47 |
| 3 | 67 | 100 | 1.50 |

The invention claimed is:

1. A nucleic acid construct comprising a first nucleotide sequence encoding a signal peptide operably linked to a second nucleotide sequence encoding a polypeptide, wherein the first nucleotide sequence is foreign to the second nucleotide sequence, and the 3' end of the first nucleotide sequence is immediately upstream of the second nucleotide sequence, and the first nucleotide sequence is selected from the group consisting of:
(a) a nucleotide sequence encoding a signal peptide having an amino acid sequence which has at least 80% identity with SEQ ID NO:1; and
(b) a nucleotide sequence having at least 80% identity with the sequence shown in positions 575 to 661 of SEQ ID NO:10.

2. The nucleic acid construct of claim 1, wherein the first nucleotide sequence is selected from the group consisting of:
(a) a nucleotide sequence encoding a signal peptide having an amino acid sequence which has at least 85% identity with SEQ ID NO: 1; and
(b) a nucleotide sequence having at least 85% identity with the sequence shown in positions 575 to 661 of SEQ ID NO:10.

3. The nucleic acid construct of claim 1, wherein the first nucleotide sequence is selected from the group consisting of:
(a) a nucleotide sequence encoding a signal peptide having an amino acid sequence which has at least 90% identity with SEQ ID NO:1; and
(b) a nucleotide sequence having at least 90% identity with the sequence shown in positions 575 to 661 of SEQ ID NO:10.

4. The nucleic acid construct of claim 1, wherein the first nucleotide sequence is selected from the group consisting of:
(a) a nucleotide sequence encoding a signal peptide having an amino acid sequence which has at least 95% identity with SEQ ID NO:1; and
(b) a nucleotide sequence having at least 95% identity with the sequence shown in positions 575 to 661 of SEQ ID NO: 10.

5. The nucleic acid construct of claim 1, wherein the first nucleotide sequence hybridizes under stringency conditions with a polynucleotide having the nucleotide sequence shown in positions 575-661 of SEQ ID NO:10, or its complementary strand, wherein the stringency conditions are defined as prehybridization, hybridization, and washing post-hybridization at 5° C. to 10° C. below the calculated Tm in 0.9 M NaCl, 0.09 M Tris-HCI pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm.

6. The nucleic acid construct of claim 1, wherein the first nucleotide sequence encodes a signal peptide comprising the amino acid sequence of SEQ ID NO:1.

7. The nucleic acid construct of claim 1, wherein the first nucleotide sequence encodes a signal peptide consisting of the amino acid sequence of SEQ ID NO:1.

8. The nucleic acid construct of claim 1, wherein the first nucleotide sequence encodes a signal peptide comprising the amino acid sequence of SEQ ID NO: 10.

9. The nucleic acid construct of claim 1, wherein the first nucleotide sequence encodes a signal peptide consisting of the amino acid sequence of SEQ ID NO: 10.

10. The nucleic acid construct of claim 1, wherein the first nucleotide sequence encodes a signal peptide which is a fragment of the amino acid sequence of SEQ ID NO: 1, which retains the ability to direct the polypeptide into or across a cell membrane.

11. The nucleic acid construct of claim 1, wherein the first nucleotide sequence consists of positions 575-661 of SEQ ID NO: 10.

12. The nucleic acid construct of claim 1, wherein the first nucleotide sequence is a subsequence of positions 575-661 of SEQ ID NO: 10, which encodes a signal peptide that retains the ability to direct the polypeptide into or across a cell membrane.

13. A recombinant Gram-positive host cell comprising the nucleic acid construct of claim 1.

14. A recombinant Gram-positive host cell comprising the nucleic acid construct of claim 2.

15. A recombinant Gram-positive host cell comprising the nucleic acid construct of claim 3.

16. A recombinant Gram-positive host cell comprising the nucleic acid construct of claim 4.

17. A recombinant Gram-positive host cell comprising the nucleic acid construct of claim 8.

18. A recombinant Gram-positive host cell comprising the nucleic acid construct of claim 11.

19. A recombinant Gram-positive host cell comprising the nucleic acid construct of claim 11.

20. A method for producing a secreted polypeptide, comprising:
  (a) cultivating a recombinant Gram-positive host cell of claim 13 in a medium conducive for the production of the polypeptide; and
  (b) recovering the secreted polypeptide from the cultivation medium.

21. A method for producing a secreted polypeptide, comprising:
  (a) cultivating a recombinant Gram-positive host cell of claim 14 in a medium conducive for the production of the polypeptide; and
  (b) recovering the secreted polypeptide from the cultivation medium.

22. A method for producing a secreted polypeptide, comprising:
  (a) cultivating a recombinant Gram-positive host cell of claim 15 in a medium conducive for the production of the polypeptide; and
  (b) recovering the secreted polypeptide from the cultivation medium.

23. A method for producing a secreted polypeptide, comprising:
  (a) cultivating a recombinant Gram-positive host cell of claim 16 in a medium conducive for the production of the polypeptide; and
  (b) recovering the secreted polypeptide from the cultivation medium.

24. A method for producing a secreted polypeptide, comprising:
  (a) cultivating a recombinant Gram-positive host cell of claim 17 in a medium conducive for the production of the polypeptide; and
  (b) recovering the secreted polypeptide from the cultivation medium.

25. A method for producing a secreted polypeptide, comprising:
  (a) cultivating a recombinant Gram-positive host cell of claim 18 in a medium conducive for the production of the polypeptide; and
  (b) recovering the secreted polypeptide from the cultivation medium.

26. A method for producing a secreted polypeptide, comprising:
  (a) cultivating a recombinant Gram-positive host cell of claim 19 in a medium conducive for the production of the polypeptide; and
  b) recovering the secreted polypeptide from the cultivation medium.

27. The method of claim 20, wherein the second nucleotide sequence encodes a polypeptide native to the host cell.

28. The method of claim 20, wherein the second nucleotide sequence encodes a polypeptide heterologous to the host cell.

29. The method of claim 20, wherein the host cell contains one or more copies of the second nucleotide sequence.

30. The method of claim 20, wherein the Gram-positive host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis* or a *Bacillus thuringiensis* cell.

* * * * *

SEQUENCE LISTING

```
<160> NUMBER OF SEQ ID NOS: 17

<210> SEQ ID NO 1
<211> LENGTH: 28
<212> TYPE: PRT
<213> ORGANISM: Artificial sequence
<220> FEATURE:
<223> OTHER INFORMATION: Hybrid LQ2 signal peptide

<400> SEQUENCE: 1

Met Lys Gln Gln Lys Arg Leu Tyr Ala Arg Leu Val Leu Met Cys Thr
1               5                   10                  15

Leu Leu Phe Val Ser Leu Pro Ile Thr Lys Thr Ser
            20                  25

<210> SEQ ID NO 2
<211> LENGTH: 47
<212> TYPE: DNA
<213> ORGANISM: Artificial sequence
<220> FEATURE:
<223> OTHER INFORMATION: Primer 067827
```

```
<400> SEQUENCE: 2
gagctccaca ttgaaagggg aggagaatca tgaaaaagaa aacgctt                    47

<210> SEQ ID NO 3
<211> LENGTH: 24
<212> TYPE: DNA
<213> ORGANISM: Artificial sequence
<220> FEATURE:
<223> OTHER INFORMATION: Primer 067828

<400> SEQUENCE: 3
acgcgtctag ttttgccacg taac                                             24

<210> SEQ ID NO 4
<211> LENGTH: 27
<212> TYPE: DNA
<213> ORGANISM: Artificial sequence
<220> FEATURE:
<223> OTHER INFORMATION: Primer 998291

<400> SEQUENCE: 4
gagctccaca ttgaaagggg aggagaa                                          27

<210> SEQ ID NO 5
<211> LENGTH: 28
<212> TYPE: DNA
<213> ORGANISM: Artificial sequence
<220> FEATURE:
<223> OTHER INFORMATION: Primer 067830

<400> SEQUENCE: 5
ggaactgctg gctgatgttt ttgtaatc                                         28

<210> SEQ ID NO 6
<211> LENGTH: 28
<212> TYPE: DNA
<213> ORGANISM: Artificial sequence
<220> FEATURE:
<223> OTHER INFORMATION: Primer 067829

<400> SEQUENCE: 6
acatcagcca gcagttccgc aagcgtca                                         28

<210> SEQ ID NO 7
<211> LENGTH: 24
<212> TYPE: DNA
<213> ORGANISM: Artificial sequence
<220> FEATURE:
<223> OTHER INFORMATION: Primer 067828

<400> SEQUENCE: 7
acgcgtctag ttttgccacg taac                                             24

<210> SEQ ID NO 8
<211> LENGTH: 7080
<212> TYPE: DNA
<213> ORGANISM: Artificial sequence
<220> FEATURE:
<223> OTHER INFORMATION: Plasmid pAEB802
<220> FEATURE:
<221> NAME/KEY: CDS
<222> LOCATION: (575)..(2110)
<223> OTHER INFORMATION: Encodes FB024 with native signal peptide
<220> FEATURE:
<221> NAME/KEY: sig_peptide
<222> LOCATION: (575)..(658)
<220> FEATURE:
```

```
<221> NAME/KEY: mat_peptide
<222> LOCATION: (659)..(2110)

<400> SEQUENCE: 8
gaattcagat ctaaagataa tatctttgaa ttgtaacccc cctcaaaagt aagaactaca      60 aaaaagaat acgttatata gaaatatgtt tgaaccttct tcagattaca aatatattcg     120
gacggactct acctcaaatg cttatctaac tatagaatga catacaagca caaccttgaa     180
aatttgaaaa tataactacc aatgaacttg ttcatgtgaa ttatcgctgt atttaatttt     240
ctcaattcaa tatataatat gccaatacat tgttacaagt agaaattaag acacccttga     300
tagccttact atacctaaca tgatgtagta ttaaatgaat atgtaaatat atttatgata     360
agaagcgact tatttataat cattacatat ttttctattg gaatgattaa gattccaata     420
gaatagtgta taaattattt atcttgaaag gagggatggc taaaaacgaa gaacattaaa     480
aacatatatt tgcaccgtct aatggattta tgaaaaatca ttttatcagt ttgaaaatta     540
tgtattatgg ccacattgaa aggggaggag aatc atg aaa caa caa aaa cgg ctt    595
                                     Met Lys Gln Gln Lys Arg Leu
                                                           -25 tac gcc cga ttg ctg acg ctg tta ttt gcg ctc atc ttc ttg ctg cct       643
Tyr Ala Arg Leu Leu Thr Leu Leu Phe Ala Leu Ile Phe Leu Leu Pro
    -20             -15                 -10 cat tct gca gca gcg gcg gta aat ggc acg ctg atg cag tat ttt gaa       691
His Ser Ala Ala Ala Ala Val Asn Gly Thr Leu Met Gln Tyr Phe Glu
-5          -1   1              5                  10 tgg tat acg ccg aac gac ggc cag cat tgg aaa cga ttg cag aat gat       739
Trp Tyr Thr Pro Asn Asp Gly Gln His Trp Lys Arg Leu Gln Asn Asp
            15                  20                  25 gcg gaa cat tta tcg gat atc gga atc act gcc gtc tgg att cct ccc       787
Ala Glu His Leu Ser Asp Ile Gly Ile Thr Ala Val Trp Ile Pro Pro
        30                  35                  40 gca tac aaa gga ttg agc caa tcc gat aac gga tac gga cct tat gat       835
Ala Tyr Lys Gly Leu Ser Gln Ser Asp Asn Gly Tyr Gly Pro Tyr Asp
    45                  50                  55 ttg tat gat tta gga gaa ttc cag caa aaa ggg acg gtc aga acg aaa       883
Leu Tyr Asp Leu Gly Glu Phe Gln Gln Lys Gly Thr Val Arg Thr Lys
60                  65                  70                  75 tac ggc aca aaa tca gag ctt caa gat gcg atc ggc tca ctg cat tcc       931
Tyr Gly Thr Lys Ser Glu Leu Gln Asp Ala Ile Gly Ser Leu His Ser
                80                  85                  90 cgg aac gtc caa gta tac gga gat gtg gtt ttg aat cat aag gct ggt       979
Arg Asn Val Gln Val Tyr Gly Asp Val Val Leu Asn His Lys Ala Gly
            95                  100                 105 gct gat gca aca gaa gat gta act gcc gtc gaa gtc aat ccg gcc aat      1027
Ala Asp Ala Thr Glu Asp Val Thr Ala Val Glu Val Asn Pro Ala Asn
        110                 115                 120 aga aat cag gaa act tcg gag gaa tat caa atc aaa gcg tgg acg gat      1075
Arg Asn Gln Glu Thr Ser Glu Glu Tyr Gln Ile Lys Ala Trp Thr Asp
    125                 130                 135 ttt cgt ttt ccg ggc cgt gga aac acg tac agt gat ttt aaa tgg cat      1123
Phe Arg Phe Pro Gly Arg Gly Asn Thr Tyr Ser Asp Phe Lys Trp His
140                 145                 150                 155 tgg tat cat ttc gac gga gcg gac tgg gat gaa tcc cgg aag atc agc      1171
Trp Tyr His Phe Asp Gly Ala Asp Trp Asp Glu Ser Arg Lys Ile Ser
                160                 165                 170 cgc atc ttt aag ttt cgt ggg gaa gga aaa gct tgg aat tgg gaa gta      1219
Arg Ile Phe Lys Phe Arg Gly Glu Gly Lys Ala Trp Asn Trp Glu Val
            175                 180                 185
```

```
tca agt gaa aac ggc aac tat gac tat tta atg tat gct gat gtt gac    1267
Ser Ser Glu Asn Gly Asn Tyr Asp Tyr Leu Met Tyr Ala Asp Val Asp
        190                 195                 200 tac gac cac cct gat gtc gtg gca gag aca aaa aaa tgg ggt atc tgg    1315
Tyr Asp His Pro Asp Val Val Ala Glu Thr Lys Lys Trp Gly Ile Trp
205                 210                 215 tat gcg aat gaa ctg tca tta gac ggc ttc cgt att gat gcc gcc aaa    1363
Tyr Ala Asn Glu Leu Ser Leu Asp Gly Phe Arg Ile Asp Ala Ala Lys
220                 225                 230                 235 cat att aaa ttt tca ttt ctg cgt gat tgg gtt cag gcg gtc aga cag    1411
His Ile Lys Phe Ser Phe Leu Arg Asp Trp Val Gln Ala Val Arg Gln
            240                 245                 250 gcg acg gga aaa gaa atg ttt acg gtt gcg gag tat tgg cag aat aat    1459
Ala Thr Gly Lys Glu Met Phe Thr Val Ala Glu Tyr Trp Gln Asn Asn
                255                 260                 265 gcc ggg aaa ctc gaa aac tac ttg aat aaa aca agc ttt aat caa tcc    1507
Ala Gly Lys Leu Glu Asn Tyr Leu Asn Lys Thr Ser Phe Asn Gln Ser
                    270                 275                 280 gtg ttt gat gtt ccg ctt cat ttc aat tta cag gcg gct tcc tca caa    1555
Val Phe Asp Val Pro Leu His Phe Asn Leu Gln Ala Ala Ser Ser Gln
285                 290                 295 gga ggc gga tat gat atg agg cgt ttg ctg gac ggt acc gtt gtg tcc    1603
Gly Gly Gly Tyr Asp Met Arg Arg Leu Leu Asp Gly Thr Val Val Ser
300                 305                 310                 315 agg cat ccg gaa aag gcg gtt aca ttt gtt gaa aat cat gac aca cag    1651
Arg His Pro Glu Lys Ala Val Thr Phe Val Glu Asn His Asp Thr Gln
            320                 325                 330 ccg gga cag tca ttg gaa tcg aca gtc caa act tgg ttt aaa ccg ctt    1699
Pro Gly Gln Ser Leu Glu Ser Thr Val Gln Thr Trp Phe Lys Pro Leu
                335                 340                 345 gca tac gcc ttt att ttg aca aga gaa tcc ggt tat cct cag gtg ttc    1747
Ala Tyr Ala Phe Ile Leu Thr Arg Glu Ser Gly Tyr Pro Gln Val Phe
                    350                 355                 360 tat ggg gat atg tac ggg aca aaa ggg aca tcg cca aag gaa att ccc    1795
Tyr Gly Asp Met Tyr Gly Thr Lys Gly Thr Ser Pro Lys Glu Ile Pro
365                 370                 375 tca ctg aaa gat aat ata gag ccg att tta aaa gcg cgt aag gag tac    1843
Ser Leu Lys Asp Asn Ile Glu Pro Ile Leu Lys Ala Arg Lys Glu Tyr
380                 385                 390                 395 gca tac ggg ccc cag cac gat tat att gac cac ccg gat gtg atc gga    1891
Ala Tyr Gly Pro Gln His Asp Tyr Ile Asp His Pro Asp Val Ile Gly
            400                 405                 410 tgg acg agg gaa ggt gac agc tcc gcc gcc aaa tca ggt ttg gcc gct    1939
Trp Thr Arg Glu Gly Asp Ser Ser Ala Ala Lys Ser Gly Leu Ala Ala
                415                 420                 425 tta atc acg gac gga ccc ggc gga tca aag cgg atg tat gcc ggc ctg    1987
Leu Ile Thr Asp Gly Pro Gly Gly Ser Lys Arg Met Tyr Ala Gly Leu
                    430                 435                 440 aaa aat gcc ggc gag aca tgg tat gac ata acg ggc aac cgt tca gat    2035
Lys Asn Ala Gly Glu Thr Trp Tyr Asp Ile Thr Gly Asn Arg Ser Asp
445                 450                 455 act gta aaa atc gga tct gac ggc tgg gga gag ttt cat gta aac gat    2083
Thr Val Lys Ile Gly Ser Asp Gly Trp Gly Glu Phe His Val Asn Asp
460                 465                 470                 475 ggg tcc gtc tcc att tat gtt cag aaa taacgcgtgc tagcggccgc          2130
Gly Ser Val Ser Ile Tyr Val Gln Lys
            480 gtcgactaga agagcagaga ggacggattt cctgaaggaa atccgttttt ttattttgcc  2190 cgtcttataa atttcgttga gatctacgcg tccatgggct agcgcggccg cgtcgacagg  2250
```

```
cctctttgat tacatttat aattaatttt aacaaagtgt catcagccct caggaaggac    2310
ttgctgacag tttgaatcgc ataggtaagg cggggatgaa atggcaacgt tatctgatgt    2370
agcaaagaaa gcaaatgtgt cgaaaatgac ggtatcgcgg gtgatcaatc atcctgagac    2430
tgtgacggat gaattgaaaa agcttgttca ttccgcaatg aaggagctca attatatacc    2490
gaactatgca gcaagagcgc tcgttcaaaa cagaacacag gtcgtcaagc tgctcatact    2550
ggaagaaatg gatacaacag aaccttatta tatgaatctg ttaacgggaa tcagccgcga    2610
gctggaccgt catcattatg ctttgcagct tgtcacaagg aaatctctca atatcggcca    2670
gtgcgacggc attattgcga cggggttgag aaaagccgat tttgaagggc tcatcaaggt    2730
ttttgaaaag cgtgtcgttg tattcgggac gtcgattcac aaaaataggc acgaaaaaa    2790 caagtaaggg atgcagttta tgcatcccctt aacttactta ttaaataatt tatagctatt    2850 gaaagagat aagaattgtt caaagctaat attgtttaaa tcgtcaattc ctgcatgttt    2910
taaggaattg ttaaattgat tttttgtaaa tattttcttg tattctttgt taacccattt    2970
cataacgaaa taattatact tttgtttatc tttgtgtgat attcttgatt tttttctact    3030
taatctgata agtgagctat tcactttagg tttaggatga aaatattctc ttggaaccat    3090
acttaatata gaaatatcaa cttctgccat taaaagtaat gccaatgagc gttttgtatt    3150
taataatctt ttagcaaacc cgtattccac gattaaataa atctcattag ctatactatc    3210
aaaaacaatt ttgcgtatta tatccgtact tatgttataa ggtatattac catatatttt    3270
ataggattgg ttttaggaa atttaaactg caatatatcc ttgtttaaaa cttggaaatt    3330
atcgtgatca acaagtttat tttctgtagt tttgcataat ttatggtcta tttcaatggc    3390
agttacgaaa ttcacctct ttactaattc aagggtaaaa tggccttttc ctgagccgat    3450
ttcaaagata ttatcatgtt catttaatct tatatttgtc attattttat ctatattatg    3510
ttttgaagta ataagttttt gactgtgttt tatatttttc tcgttcatta taaccctctt    3570
taatttggtt atatgaattt tgcttattaa cgattcatta taaccactta tttttgttt    3630 ggttgataat gaactgtgct gattacaaaa atactaaaaa tgcccatatt tttcctcct    3690 tataaaatta gtataattat agcacgagct ctgataaata tgaacatgat gagtgatcgt    3750
taaatttata ctgcaatcgg atgcgattat tgaataaaag atatgagaga tttatctaat    3810 ttctttttc ttgtaaaaaa agaaagttct taaaggtttt atagttttgg tcgtagagca    3870
cacggtttaa cgacttaatt acgaagtaaa taagtctagt gtgttagact ttatgaaatc    3930
tatatacgtt tatatatatt tattatccgg aggtgtagca tgtctcattc aattttgagg    3990
gttgccagag ttaaaggatc aagtaataca aacgggatac aaagacataa tcaaagagag    4050
aataaaaact ataataataa agacataaat catgaggaaa catataaaaa ttatgatttg    4110
attaacgcac aaaatataaa gtataaagat aaaattgatg aaacgattga tgagaattat    4170
tcagggaaac gtaaaattcg gtcagatgca attcgacatg tggacggact ggttacaagt    4230
gataaagatt tctttgatga tttaagcgga gaagaaatag aacgattttt taagatagc    4290 ttggagtttc tagaaaatga atacggtaag gaaaatatgc tgtatgcgac tgtccatctg    4350
gatgaaagag tcccacatat gcactttggt tttgtccctt taacagagga cgggagattg    4410
tctgcaaaag aacagttagg caacaagaaa gactttactc aattacaaga tagatttaat    4470
gagtatgtga atgagaaagg ttatgaactt gaaagaggca cgtccaaaga ggttacagaa    4530
cgagaacata aagcgatgga tcagtacaag aaagatactg tatttcataa acaggaactg    4590
```

```
caagaagtta aggatgagtt acagaaggca aataagcagt tacagagtgg aatagagcat   4650
atgaggtcta cgaaaccctt tgattatgaa aatgagcgta caggtttgtt ctctggacgt   4710
gaagagactg gtagaaagat attaactgct gatgaatttg aacgcctgca agaaacaatc   4770
tcttctgcag aacggattgt tgatgattac gaaaatatta agagcacaga ctattacaca   4830
gaaaatcaag aattaaaaaa acgtagagag agtttgaaag aagtagtgaa tacatggaaa   4890
gaggggtatc acgaaaaaag taaagaggtt aataaattaa agcgagagaa tgatagtttg   4950
aatgagcagt tgaatgtatc agagaaattt caagctagta cagtgacttt atatcgtgct   5010
gcgagggcga atttccctgg gtttgagaaa gggtttaata ggcttaaaga gaaattcttt   5070
aatgattcca aatttgagcg tgtgggacag tttatggatg ttgtacagga taatgtccag   5130
aaggtcgata gaaagcgtga gaaacagcgt acagacgatt tagagatgta gaggtacttt   5190
tatgccgaga aaactttttg cgtgtgacag tccttaaaat atacttagag cgtaagcgaa   5250
agtagtagcg acagctatta actttcggtt tcaaagctct aggatttta atggacgcag    5310
cgcatcacac gcaaaaagga aattggaata aatgcgaaat ttgagatgtt aattaaagac   5370
cttttttgagg tctttttttc ttagattttt ggggttattt aggggagaaa catagggggg   5430
gtactacgac ctccccccta ggtgtccatt gtccattgtc caaacaaata aataaatatt   5490
gggttttaa tgttaaaagg ttgtttttta tgttaaagtg aaaaaaacag atgttgggag    5550
gtacagtgat ggttgtagat agaaaagaag agaaaaagt tgctgttact ttaagactta    5610
caacagaaga aaatgagata ttaaatagaa tcaagaaaaa atataatatt agcaaatcag   5670
atgcaaccgg tattctaata aaaaaatatg caaaggagga atacggtgca ttttaaacaa   5730
aaaaagatag acagcactgg catgctgcct atctatgact aaattttgtt aagtgtatta   5790
gcaccgttat tatatcatga gcgaaaatgt aataaaagaa actgaaaaca agaaaaattc   5850
aagaggacgt aattggacat ttgttttata tccagaatca gcaaaagccg agtggttaga   5910
gtatttaaaa gagttacaca ttcaatttgt agtgtctcca ttacatgata gggatactga   5970
tacagaaggt aggatgaaaa aagagcatta tcatattcta gtgatgtatg agggtaataa   6030
atcttatgaa cagataaaaa taattacaga agaattgaat gcgactattc cgcagattgc   6090
aggaagtgtg aaaggtcttg tgagatatat gcttcacatg gacgatccta ataaatttaa   6150
atatcaaaaa gaagatatga tagtttatgg cggtgtagag gttgatgaat tattaaagaa   6210
aacaacaaca gatagatata aattaattaa agaaatgatt gagtttattg atgaacaagg   6270
aatcgtagaa tttaagagtt taatggatta tgcaatgaag tttaaatttg atgattggtt   6330
cccgctttta tgtgataact cggcgtatgt tattcaagaa tatataaaat caaatcggta   6390
taaatctgac cgatagattt tgaatttagg tgtcacaaga cactcttttt tcgcaccagc   6450
gaaaactggt ttaagccgac tgcgcaaaag acataatcga ctctagagga tccccgggta   6510
ccgagctctg ccttttagtc cagctgattt cacttttttgc attctacaaa ctgcataact   6570
catatgtaaa tcgctccttt ttaggtggca caaatgtgag gcattttcgc tctttccggc   6630
aaccacttcc aagtaaagta taacacacta tactttatat tcataaagtg tgtgctctgc   6690
gaggctgtcg gcagtgccga ccaaaaccat aaaacccttta agacctttct tttttttacg   6750
agaaaaaaga aacaaaaaaa cctgccctct gccacctcag caagggggg ttttgctctc    6810
gtgctcgttt aaaaatcagc aagggacagg tagtattttt tgagaagatc actcaaaaaa   6870
tctccaccctt taaccccttg ccaattttta ttttgtccgt tttgtctagc ttaccgaaag   6930
ccagactcag caagaataaa atttttattg tctttcggtt ttctagtgta acggacaaaa   6990
```

-continued

```
ccactcaaaa taaaaaagat acaagagagg tctctcgtat cttttattca gcaatcgcgc    7050
ccgattgctg aacagattaa taatgagctc                                     7080
```

<210> SEQ ID NO 9
<211> LENGTH: 512
<212> TYPE: PRT
<213> ORGANISM: Artificial sequence
<220> FEATURE:
<223> OTHER INFORMATION: Synthetic Construct

<400> SEQUENCE: 9

```
Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Val Asn Gly
        -10                  -5              -1   1

Thr Leu Met Gln Tyr Phe Glu Trp Tyr Thr Pro Asn Asp Gly Gln His
  5              10                  15                  20

Trp Lys Arg Leu Gln Asn Asp Ala Glu His Leu Ser Asp Ile Gly Ile
             25                  30                  35

Thr Ala Val Trp Ile Pro Pro Ala Tyr Lys Gly Leu Ser Gln Ser Asp
             40                  45                  50

Asn Gly Tyr Gly Pro Tyr Asp Leu Tyr Asp Leu Gly Glu Phe Gln Gln
             55                  60                  65

Lys Gly Thr Val Arg Thr Lys Tyr Gly Thr Lys Ser Glu Leu Gln Asp
             70                  75                  80

Ala Ile Gly Ser Leu His Ser Arg Asn Val Gln Val Tyr Gly Asp Val
85                   90                  95                 100

Val Leu Asn His Lys Ala Gly Ala Asp Ala Thr Glu Asp Val Thr Ala
                105                 110                 115

Val Glu Val Asn Pro Ala Asn Arg Asn Gln Glu Thr Ser Glu Glu Tyr
                120                 125                 130

Gln Ile Lys Ala Trp Thr Asp Phe Arg Phe Pro Gly Arg Gly Asn Thr
            135                 140                 145

Tyr Ser Asp Phe Lys Trp His Trp Tyr His Phe Asp Gly Ala Asp Trp
            150                 155                 160

Asp Glu Ser Arg Lys Ile Ser Arg Ile Phe Lys Phe Arg Gly Glu Gly
165                 170                 175                 180

Lys Ala Trp Asn Trp Glu Val Ser Ser Glu Asn Gly Asn Tyr Asp Tyr
                185                 190                 195

Leu Met Tyr Ala Asp Val Asp Tyr Asp His Pro Asp Val Val Ala Glu
            200                 205                 210

Thr Lys Lys Trp Gly Ile Trp Tyr Ala Asn Glu Leu Ser Leu Asp Gly
            215                 220                 225

Phe Arg Ile Asp Ala Ala Lys His Ile Lys Phe Ser Phe Leu Arg Asp
            230                 235                 240

Trp Val Gln Ala Val Arg Gln Ala Thr Gly Lys Glu Met Phe Thr Val
245                 250                 255                 260

Ala Glu Tyr Trp Gln Asn Asn Ala Gly Lys Leu Glu Asn Tyr Leu Asn
                265                 270                 275

Lys Thr Ser Phe Asn Gln Ser Val Phe Asp Val Pro Leu His Phe Asn
            280                 285                 290

Leu Gln Ala Ala Ser Ser Gln Gly Gly Gly Tyr Asp Met Arg Arg Leu
            295                 300                 305

Leu Asp Gly Thr Val Val Ser Arg His Pro Glu Lys Ala Val Thr Phe
```

```
Val Glu Asn His Asp Thr Gln Pro Gly Gln Ser Leu Glu Ser Thr Val
325                 330                 335                 340

Gln Thr Trp Phe Lys Pro Leu Ala Tyr Ala Phe Ile Leu Thr Arg Glu
            345                 350                 355

Ser Gly Tyr Pro Gln Val Phe Tyr Gly Asp Met Tyr Gly Thr Lys Gly
                360                 365                 370

Thr Ser Pro Lys Glu Ile Pro Ser Leu Lys Asp Asn Ile Glu Pro Ile
        375                 380                 385

Leu Lys Ala Arg Lys Glu Tyr Ala Tyr Gly Pro Gln His Asp Tyr Ile
    390                 395                 400

Asp His Pro Asp Val Ile Gly Trp Thr Arg Glu Gly Asp Ser Ser Ala
405                 410                 415                 420

Ala Lys Ser Gly Leu Ala Ala Leu Ile Thr Asp Gly Pro Gly Gly Ser
            425                 430                 435

Lys Arg Met Tyr Ala Gly Leu Lys Asn Ala Gly Glu Thr Trp Tyr Asp
                440                 445                 450

Ile Thr Gly Asn Arg Ser Asp Thr Val Lys Ile Gly Ser Asp Gly Trp
        455                 460                 465

Gly Glu Phe His Val Asn Asp Gly Ser Val Ser Ile Tyr Val Gln Lys
    470                 475                 480
```

<210> SEQ ID NO 10
<211> LENGTH: 7080
<212> TYPE: DNA
<213> ORGANISM: Artificial sequence
<220> FEATURE:
<223> OTHER INFORMATION: pAEB909
<220> FEATURE:
<221> NAME/KEY: CDS
<222> LOCATION: (575)..(2110)
<223> OTHER INFORMATION: Encoding mature FB024 with the hybrid LQ2
    signal peptide
<220> FEATURE:
<221> NAME/KEY: sig_peptide
<222> LOCATION: (575)..(661)
<220> FEATURE:
<221> NAME/KEY: mat_peptide
<222> LOCATION: (662)..(2110)

<400> SEQUENCE: 10

```
gaattcagat ctaaagataa tatctttgaa ttgtaacccc cctcaaaagt aagaactaca      60 aaaaagaat acgttatata gaaatatgtt tgaaccttct tcagattaca aatatattcg     120
gacggactct acctcaaatg cttatctaac tatagaatga catacaagca caaccttgaa    180
aatttgaaaa tataactacc aatgaacttg ttcatgtgaa ttatcgctgt atttaatttt    240
ctcaattcaa tatataatat gccaatacat tgttacaagt agaaattaag acacccttga    300
tagccttact atacctaaca tgatgtagta ttaaatgaat atgtaaatat atttatgata    360
agaagcgact tatttataat cattacatat ttttctattg gaatgattaa gattccaata    420
gaatagtgta taaattattt atcttgaaag gagggatggc taaaaacgaa gaacattaaa    480
aacatatatt tgcaccgtct aatggattta tgaaaaatca ttttatcagt ttgaaaatta    540
tgtattatgg ccacattgaa aggggaggag aatc atg aaa caa caa aaa cgg ctt    595
                                     Met Lys Gln Gln Lys Arg Leu
                                                         -25 tac gcc cga ttg gtg ctt atg tgc acg ctg tta ttt gtc agt ttg ccg      643
Tyr Ala Arg Leu Val Leu Met Cys Thr Leu Leu Phe Val Ser Leu Pro
    -20                 -15                 -10
```

```
att aca aaa aca tca gcc gta aat ggc acg ctg atg cag tat ttt gaa    691
Ile Thr Lys Thr Ser Ala Val Asn Gly Thr Leu Met Gln Tyr Phe Glu
    -5          -1   1               5                      10 tgg tat acg ccg aac gac ggc cag cat tgg aaa cga ttg cag aat gat    739
Trp Tyr Thr Pro Asn Asp Gly Gln His Trp Lys Arg Leu Gln Asn Asp
            15                  20                  25 gcg gaa cat tta tcg gat atc gga atc act gcc gtc tgg att cct ccc    787
Ala Glu His Leu Ser Asp Ile Gly Ile Thr Ala Val Trp Ile Pro Pro
            30                  35                  40 gca tac aaa gga ttg agc caa tcc gat aac gga tac gga cct tat gat    835
Ala Tyr Lys Gly Leu Ser Gln Ser Asp Asn Gly Tyr Gly Pro Tyr Asp
            45                  50                  55 ttg tat gat tta gga gaa ttc cag caa aaa ggg acg gtc aga acg aaa    883
Leu Tyr Asp Leu Gly Glu Phe Gln Gln Lys Gly Thr Val Arg Thr Lys
            60                  65                  70 tac ggc aca aaa tca gag ctt caa gat gcg atc ggc tca ctg cat tcc    931
Tyr Gly Thr Lys Ser Glu Leu Gln Asp Ala Ile Gly Ser Leu His Ser
75              80                  85                  90 cgg aac gtc caa gta tac gga gat gtg gtt ttg aat cat aag gct ggt    979
Arg Asn Val Gln Val Tyr Gly Asp Val Val Leu Asn His Lys Ala Gly
                95                  100                 105 gct gat gca aca gaa gat gta act gcc gtc gaa gtc aat ccg gcc aat   1027
Ala Asp Ala Thr Glu Asp Val Thr Ala Val Glu Val Asn Pro Ala Asn
            110                 115                 120 aga aat cag gaa act tcg gag gaa tat caa atc aaa gcg tgg acg gat   1075
Arg Asn Gln Glu Thr Ser Glu Glu Tyr Gln Ile Lys Ala Trp Thr Asp
            125                 130                 135 ttt cgt ttt ccg ggc cgt gga aac acg tac agt gat ttt aaa tgg cat   1123
Phe Arg Phe Pro Gly Arg Gly Asn Thr Tyr Ser Asp Phe Lys Trp His
140                 145                 150 tgg tat cat ttc gac gga gcg gac tgg gat gaa tcc cgg aag atc agc   1171
Trp Tyr His Phe Asp Gly Ala Asp Trp Asp Glu Ser Arg Lys Ile Ser
155             160                 165                 170 cgc atc ttt aag ttt cgt ggg gaa gga aaa gct tgg aat tgg gaa gta   1219
Arg Ile Phe Lys Phe Arg Gly Glu Gly Lys Ala Trp Asn Trp Glu Val
            175                 180                 185 tca agt gaa aac ggc aac tat gac tat tta atg tat gct gat gtt gac   1267
Ser Ser Glu Asn Gly Asn Tyr Asp Tyr Leu Met Tyr Ala Asp Val Asp
            190                 195                 200 tac gac cac cct gat gtc gtg gca gag aca aaa aaa tgg ggt atc tgg   1315
Tyr Asp His Pro Asp Val Val Ala Glu Thr Lys Lys Trp Gly Ile Trp
            205                 210                 215 tat gcg aat gaa ctg tca tta gac ggc ttc cgt att gat gcc gcc aaa   1363
Tyr Ala Asn Glu Leu Ser Leu Asp Gly Phe Arg Ile Asp Ala Ala Lys
220                 225                 230 cat att aaa ttt tca ttt ctg cgt gat tgg gtt cag gcg gtc aga cag   1411
His Ile Lys Phe Ser Phe Leu Arg Asp Trp Val Gln Ala Val Arg Gln
235             240                 245                 250 gcg acg gga aaa gaa atg ttt acg gtt gcg gag tat tgg cag aat aat   1459
Ala Thr Gly Lys Glu Met Phe Thr Val Ala Glu Tyr Trp Gln Asn Asn
            255                 260                 265 gcc ggg aaa ctc gaa aac tac ttg aat aaa aca agc ttt aat caa tcc   1507
Ala Gly Lys Leu Glu Asn Tyr Leu Asn Lys Thr Ser Phe Asn Gln Ser
            270                 275                 280 gtg ttt gat gtt ccg ctt cat ttc aat tta cag gcg gct tcc tca caa   1555
Val Phe Asp Val Pro Leu His Phe Asn Leu Gln Ala Ala Ser Ser Gln
            285                 290                 295 gga ggc gga tat gat atg agg cgt ttg ctg gac ggt acc gtt gtg tcc   1603
Gly Gly Gly Tyr Asp Met Arg Arg Leu Leu Asp Gly Thr Val Val Ser
300                 305                 310
```

```
agg cat ccg gaa aag gcg gtt aca ttt gtt gaa aat cat gac aca cag    1651
Arg His Pro Glu Lys Ala Val Thr Phe Val Glu Asn His Asp Thr Gln
315             320                 325                 330 ccg gga cag tca ttg gaa tcg aca gtc caa act tgg ttt aaa ccg ctt    1699
Pro Gly Gln Ser Leu Glu Ser Thr Val Gln Thr Trp Phe Lys Pro Leu
                335                 340                 345 gca tac gcc ttt att ttg aca aga gaa tcc ggt tat cct cag gtg ttc    1747
Ala Tyr Ala Phe Ile Leu Thr Arg Glu Ser Gly Tyr Pro Gln Val Phe
            350                 355                 360 tat ggg gat atg tac ggg aca aaa ggg aca tcg cca aag gaa att ccc    1795
Tyr Gly Asp Met Tyr Gly Thr Lys Gly Thr Ser Pro Lys Glu Ile Pro
        365                 370                 375 tca ctg aaa gat aat ata gag ccg att tta aaa gcg cgt aag gag tac    1843
Ser Leu Lys Asp Asn Ile Glu Pro Ile Leu Lys Ala Arg Lys Glu Tyr
    380                 385                 390 gca tac ggg ccc cag cac gat tat att gac cac ccg gat gtg atc gga    1891
Ala Tyr Gly Pro Gln His Asp Tyr Ile Asp His Pro Asp Val Ile Gly
395                 400                 405                 410 tgg acg agg gaa ggt gac agc tcc gcc gcc aaa tca ggt ttg gcc gct    1939
Trp Thr Arg Glu Gly Asp Ser Ser Ala Ala Lys Ser Gly Leu Ala Ala
                415                 420                 425 tta atc acg gac gga ccc ggc gga tca aag cgg atg tat gcc ggc ctg    1987
Leu Ile Thr Asp Gly Pro Gly Gly Ser Lys Arg Met Tyr Ala Gly Leu
            430                 435                 440 aaa aat gcc ggc gag aca tgg tat gac ata acg ggc aac cgt tca gat    2035
Lys Asn Ala Gly Glu Thr Trp Tyr Asp Ile Thr Gly Asn Arg Ser Asp
        445                 450                 455 act gta aaa atc gga tct gac ggc tgg gga gag ttt cat gta aac gat    2083
Thr Val Lys Ile Gly Ser Asp Gly Trp Gly Glu Phe His Val Asn Asp
    460                 465                 470 ggg tcc gtc tcc att tat gtt cag aaa taacgcgtgc tagcggccgc         2130
Gly Ser Val Ser Ile Tyr Val Gln Lys
475                 480 gtcgactaga agagcagaga ggacggattt cctgaaggaa atccgttttt ttattttgcc   2190
cgtcttataa atttcgttga gatctacgcg tccatgggct agcgcggccg cgtcgacagg   2250
cctctttgat tacattttat aattaatttt aacaaagtgt catcagccct caggaaggac   2310
ttgctgacag tttgaatcgc ataggtaagg cggggatgaa atggcaacgt tatctgatgt   2370
agcaaagaaa gcaatgtgt cgaaaatgac ggtatcgcgg gtgatcaatc atcctgagac   2430
tgtgacggat gaattgaaaa agcttgttca ttccgcaatg aaggagctca attatatacc   2490
gaactatgca gcaagagcgc tcgttcaaaa cagaacacag gtcgtcaagc tgctcatact   2550
ggaagaaatg gatacaacag aaccttatta tatgaatctg ttaacgggaa tcagccgcga   2610
gctggaccgt catcattatg ctttgcagct tgtcacaagg aaatctctca atatcggcca   2670
gtgcgacggc attattgcga cggggttgag aaaagccgat tttgaagggc tcatcaaggt   2730
ttttgaaaag cgtgtcgttg tattcgggac gtcgattcac aaaaataggc acacgaaaaa   2790
caagtaaggg atgcagttta tgcatcccctt aacttactta ttaaataatt tatagctatt   2850
gaaaagagat aagaattgtt caaagctaat attgtttaaa tcgtcaattc ctgcatgttt   2910
taaggaattg ttaaattgat ttttttgtaaa tattttcttg tattctttgt taacccattt   2970
cataacgaaa taattatact tttgtttatc tttgtgtgat attcttgatt ttttctact    3030 taatctgata agtgagctat tcactttagg tttaggatga aaatattctc ttggaaccat   3090
acttaatata gaaatatcaa cttctgccat taaaagtaat gccaatgagc gttttgtatt   3150
```

```
taataatctt ttagcaaacc cgtattccac gattaaataa atctcattag ctatactatc    3210
aaaaacaatt ttgcgtatta tatccgtact tatgttataa ggtatattac catatatttt    3270
ataggattgg ttttaggaa atttaaactg caatatatcc ttgtttaaaa cttggaaatt    3330
atcgtgatca acaagtttat tttctgtagt tttgcataat ttatggtcta tttcaatggc    3390
agttacgaaa ttacacctct ttactaattc aagggtaaaa tggccttttc ctgagccgat    3450
ttcaaagata ttatcatgtt catttaatct tatatttgtc attattttat ctatattatg    3510
ttttgaagta ataaagtttt gactgtgttt tatattttc tcgttcatta taaccctctt    3570
taatttggtt atatgaattt tgcttattaa cgattcatta taaccactta ttttttgttt    3630
ggttgataat gaactgtgct gattacaaaa atactaaaaa tgcccatatt ttttcctcct    3690
tataaaatta gtataattat agcacgagct ctgataaata tgaacatgat gagtgatcgt    3750
taaatttata ctgcaatcgg atgcgattat tgaataaaag atatgagaga tttatctaat    3810
ttcttttttc ttgtaaaaaa agaaagttct taaaggtttt atagttttgg tcgtagagca    3870
cacggtttaa cgacttaatt acgaagtaaa taagtctagt gtgttagact ttatgaaatc    3930
tatatacgtt tatatatatt tattatccgg aggtgtagca tgtctcattc aatttttgagg    3990 gttgccagag ttaaaggatc aagtaataca aacgggatac aaagacataa tcaaagagag    4050
aataaaaact ataataataa agacataaat catgaggaaa catataaaaa ttatgatttg    4110
attaacgcac aaaatataaa gtataaagat aaaattgatg aaacgattga tgagaattat    4170
tcagggaaac gtaaaattcg gtcagatgca attcgacatg tggacggact ggttacaagt    4230
gataaagatt tctttgatga tttaagcgga gaagaaatag aacgattttt taaagatagc    4290
ttggagtttc tagaaaatga atacggtaag gaaaatatgc tgtatgcgac tgtccatctg    4350
gatgaaagag tcccacatat gcactttggt tttgtcccct taacagagga cgggagattg    4410
tctgcaaaag aacagttagg caacaagaaa gactttactc aattacaaga tagatttaat    4470
gagtatgtga atgagaaagg ttatgaactt gaaagaggca cgtccaaaga ggttacagaa    4530
cgagaacata aagcgatgga tcagtacaag aaagatactg tatttcataa acaggaactg    4590
caagaagtta aggatgagtt acagaaggca aataagcagt tacagagtgg aatagagcat    4650
atgaggtcta cgaaacccct tgattatgaa aatgagcgta caggtttgtt ctctggacgt    4710
gaagagactg gtagaaagat attaactgct gatgaatttg aacgcctgca agaaacaatc    4770
tcttctgcag aacggattgt tgatgattac gaaaatatta agagcacaga ctattacaca    4830
gaaaatcaag aattaaaaaa acgtagagag agtttgaaag aagtagtgaa tacatggaaa    4890 gagggggtatc acgaaaaaag taaagaggtt aataaattaa agcgagagaa tgatagtttg    4950
aatgagcagt tgaatgtatc agagaaattt caagctagta cagtgacttt atatcgtgct    5010
gcgagggcga atttccctgg gtttgagaaa gggtttaata ggcttaaaga gaaattcttt    5070
aatgattcca aatttgagcg tgtgggacag tttatggatg ttgtacagga taatgtccag    5130
aaggtcgata gaaagcgtga gaaacagcgt acagacgatt tagagatgta gaggtacttt    5190
tatgccgaga aaactttttg cgtgtgacag tccttaaaat atacttagag cgtaagcgaa    5250
agtagtagcg acagctatta actttcggtt tcaaagctct aggattttta atggacgcag    5310
cgcatcacac gcaaaaagga aattggaata aatgcgaaat ttgagatgtt aattaaagac    5370 cttttttgagg tctttttttc ttagattttt ggggttattt aggggagaaa acatagggggg    5430 gtactacgac ctcccccccta ggtgtccatt gtccattgtc caaacaaata aataaatatt    5490 gggttttttaa tgttaaaagg ttgttttttta tgttaaagtg aaaaaaacag atgttgggag    5550
```

```
gtacagtgat ggttgtagat agaaaagaag agaaaaaagt tgctgttact ttaagactta    5610
caacagaaga aaatgagata ttaaatagaa tcaaagaaaa atataatatt agcaaatcag    5670
atgcaaccgg tattctaata aaaaaatatg caaaggagga atacggtgca ttttaaacaa    5730
aaaaagatag acagcactgg catgctgcct atctatgact aaattttgtt aagtgtatta    5790
gcaccgttat tatatcatga gcgaaaatgt aataaaagaa actgaaaaca gaaaaattc     5850
aagaggacgt aattggacat ttgttttata tccagaatca gcaaaagccg agtggttaga    5910
gtatttaaaa gagttacaca ttcaatttgt agtgtctcca ttacatgata gggatactga    5970
tacagaaggt aggatgaaaa aagagcatta tcatattcta gtgatgtatg agggtaataa    6030
atcttatgaa cagataaaaa taattacaga agaattgaat gcgactattc cgcagattgc    6090
aggaagtgtg aaaggtcttg tgagatatat gcttcacatg gacgatccta ataaatttaa    6150
atatcaaaaa gaagatatga tagtttatgg cggtgtagat gttgatgaat tattaaagaa    6210
aacaacaaca gatagatata aattaattaa agaaatgatt gagtttattg atgaacaagg    6270
aatcgtagaa tttaagagtt taatggatta tgcaatgaag tttaaatttg atgattggtt    6330
cccgctttta tgtgataact cggcgtatgt tattcaagaa tatataaaat caaatcggta    6390
taaatctgac cgatagattt tgaatttagg tgtcacaaga cactcttttt tcgcaccagc    6450
gaaaactggt ttaagccgac tgcgcaaaag acataatcga ctctagagga tccccgggta    6510
ccgagctctg cctttagtc cagctgattt cacttttgc attctacaaa ctgcataact      6570
catatgtaaa tcgctccttt ttaggtggca caaatgtgag gcattttcgc tctttccggc    6630
aaccacttcc aagtaaagta taacacacta tactttatat tcataaagtg tgtgctctgc    6690
gaggctgtcg gcagtgccga ccaaaaccat aaaaccttta agacctttct ttttttacg     6750
agaaaaaga aacaaaaaaa cctgccctct gccacctcag caaaggggg ttttgctctc     6810
gtgctcgttt aaaatcagc aagggacagg tagtattttt tgagaagatc actcaaaaaa     6870
tctccacctt taaacccttg ccaatttta ttttgtccgt tttgtctagc ttaccgaaag    6930
ccagactcag caagaataaa attttatg tctttcggtt ttctagtgta acggacaaaa      6990
ccactcaaaa taaaaagat acaagagagg tctctcgtat cttttattca gcaatcgcgc    7050
ccgattgctg aacagattaa taatgagctc                                    7080
```

<210> SEQ ID NO 11
<211> LENGTH: 512
<212> TYPE: PRT
<213> ORGANISM: Artificial sequence
<220> FEATURE:
<223> OTHER INFORMATION: Synthetic Construct

<400> SEQUENCE: 11

Met Lys Gln Gln Lys Arg Leu Tyr Ala Arg Leu Val Leu Met Cys Thr
            -25                 -20                 -15

Leu Leu Phe Val Ser Leu Pro Ile Thr Lys Thr Ser Ala Val Asn Gly
        -10                  -5                  -1   1

Thr Leu Met Gln Tyr Phe Glu Trp Tyr Thr Pro Asn Asp Gly Gln His
  5                  10                  15

Trp Lys Arg Leu Gln Asn Asp Ala Glu His Leu Ser Asp Ile Gly Ile
 20                  25                  30                  35

Thr Ala Val Trp Ile Pro Pro Ala Tyr Lys Gly Leu Ser Gln Ser Asp
                 40                  45                  50

Asn Gly Tyr Gly Pro Tyr Asp Leu Tyr Asp Leu Gly Glu Phe Gln Gln

-continued

```
                55                  60                  65
Lys Gly Thr Val Arg Thr Lys Tyr Gly Thr Lys Ser Glu Leu Gln Asp
                70                  75                  80

Ala Ile Gly Ser Leu His Ser Arg Asn Val Gln Val Tyr Gly Asp Val
 85                  90                  95

Val Leu Asn His Lys Ala Gly Ala Asp Ala Thr Glu Asp Val Thr Ala
100                 105                 110                 115

Val Glu Val Asn Pro Ala Asn Arg Asn Gln Glu Thr Ser Glu Glu Tyr
                    120                 125                 130

Gln Ile Lys Ala Trp Thr Asp Phe Arg Phe Pro Gly Arg Gly Asn Thr
                135                 140                 145

Tyr Ser Asp Phe Lys Trp His Trp Tyr His Phe Asp Gly Ala Asp Trp
                150                 155                 160

Asp Glu Ser Arg Lys Ile Ser Arg Ile Phe Lys Phe Arg Gly Glu Gly
                165                 170                 175

Lys Ala Trp Asn Trp Glu Val Ser Ser Glu Asn Gly Asn Tyr Asp Tyr
180                 185                 190                 195

Leu Met Tyr Ala Asp Val Asp Tyr Asp His Pro Asp Val Val Ala Glu
                    200                 205                 210

Thr Lys Lys Trp Gly Ile Trp Tyr Ala Asn Glu Leu Ser Leu Asp Gly
                215                 220                 225

Phe Arg Ile Asp Ala Ala Lys His Ile Lys Phe Ser Phe Leu Arg Asp
                230                 235                 240

Trp Val Gln Ala Val Arg Gln Ala Thr Gly Lys Glu Met Phe Thr Val
                245                 250                 255

Ala Glu Tyr Trp Gln Asn Asn Ala Gly Lys Leu Glu Asn Tyr Leu Asn
260                 265                 270                 275

Lys Thr Ser Phe Asn Gln Ser Val Phe Asp Val Pro Leu His Phe Asn
                    280                 285                 290

Leu Gln Ala Ala Ser Ser Gln Gly Gly Gly Tyr Asp Met Arg Arg Leu
                295                 300                 305

Leu Asp Gly Thr Val Val Ser Arg His Pro Glu Lys Ala Val Thr Phe
                310                 315                 320

Val Glu Asn His Asp Thr Gln Pro Gly Gln Ser Leu Glu Ser Thr Val
325                 330                 335

Gln Thr Trp Phe Lys Pro Leu Ala Tyr Ala Phe Ile Leu Thr Arg Glu
340                 345                 350                 355

Ser Gly Tyr Pro Gln Val Phe Tyr Gly Asp Met Tyr Gly Thr Lys Gly
                    360                 365                 370

Thr Ser Pro Lys Glu Ile Pro Ser Leu Lys Asp Asn Ile Glu Pro Ile
                375                 380                 385

Leu Lys Ala Arg Lys Glu Tyr Ala Tyr Gly Pro Gln His Asp Tyr Ile
                390                 395                 400

Asp His Pro Asp Val Ile Gly Trp Thr Arg Glu Gly Asp Ser Ser Ala
                405                 410                 415

Ala Lys Ser Gly Leu Ala Ala Leu Ile Thr Asp Gly Pro Gly Gly Ser
420                 425                 430                 435

Lys Arg Met Tyr Ala Gly Leu Lys Asn Ala Gly Glu Thr Trp Tyr Asp
                    440                 445                 450

Ile Thr Gly Asn Arg Ser Asp Thr Val Lys Ile Gly Ser Asp Gly Trp
                455                 460                 465

Gly Glu Phe His Val Asn Asp Gly Ser Val Ser Ile Tyr Val Gln Lys
                    470                 475                 480
```

<210> SEQ ID NO 12
<211> LENGTH: 33
<212> TYPE: DNA
<213> ORGANISM: Artificial sequence
<220> FEATURE:
<223> OTHER INFORMATION: Primer pab182

<400> SEQUENCE: 12
ggggacgcgt tatttctgaa cataaatgga gac        33

<210> SEQ ID NO 13
<211> LENGTH: 20
<212> TYPE: DNA
<213> ORGANISM: Artificial sequence
<220> FEATURE:
<223> OTHER INFORMATION: Primer pab322

<400> SEQUENCE: 13
gaggagaatc atgaaacaac        20

<210> SEQ ID NO 14
<211> LENGTH: 5635
<212> TYPE: DNA
<213> ORGANISM: Artificial sequence
<220> FEATURE:
<223> OTHER INFORMATION: DNA sequence of the B. licheniformis amyL
    region in AEB847.
<220> FEATURE:
<221> NAME/KEY: CDS
<222> LOCATION: (2469)..(4004)
<223> OTHER INFORMATION: Encodes FB024 with native signal peptide.
<220> FEATURE:
<221> NAME/KEY: sig_peptide
<222> LOCATION: (2469)..(2555)
<220> FEATURE:
<221> NAME/KEY: mat_peptide
<222> LOCATION: (2556)..(4004)

<400> SEQUENCE: 14
tgatcttaaa aagagcgata tccgtttgga tgaacatacg gcattctatt atacaagcag        60
cggaatttca attgtatttc agcagtatga tatcgccccg tatgcagccg gaaaccagga       120
aataaagctt ccgtcgacgc ttttatatta gccccggcat tagatctaat atttgtaata       180
gaaacagaga gagcaagtca tgaaacagga gagtgagcag cgatgtctgg caaaccatca       240
tttcgatggg ttaaaatgtt gattttttta acgatattaa taggtttggc agggtactct       300
tacaataaag tgtcaagcaa cagccaagag ccccctcagc caaaaaaaga ccgcggacaa       360
tccggcctcg gcgtcgaatc catggtcaat gacagcaaac aagagaggta tgccatccat       420
tatccggtgt ttcacataaa agaaatcgat gaacaaataa aagattatgt gaatcaagaa       480
ttggccggtt ttaaagagga taacgcaaag gcccaggctc aggatgaaga cgggcctttt       540
gaactgaaca ttaaatataa ggttgtctat tatacaaagg atacggccag tgttgtgctg       600
aatcaataca tagaggccgg cggcgtatcg ggtacaacat ctgtcaagac gtttaacgct       660
gatttaaagc agaaaaagct gctgtcccct caagatctgt ttgaagagaa ttcagatttt       720
ctgaacagga tttcaagcat tgcctatcag gaattgaaaa atcggaatcc gtctgctgac       780
atggctttat taaaagaagg gacgagccct caggaagaac atttcagccg cttcgcgctt       840
cttgaaaacg aggtggaatt ttattttgag aaaaaacaaa ccggtcttga acagtctgta       900
aaaataaaaa aagaatgggt aaaagatatt ttaaagacc gatatcagga tatgaaaaag       960
aatcgtcttc aggccaaacc tgatcaggag cctgttccgc ttccgaagca agcgaaaatt      1020

```
                                                  -continued aatcccgatg aaaaagtgat tgccctcaca tttgatgacg gtccgaatcc cgctacaacg        1080
aataaaatat taaacgcttt acagaagcat gaagggcatg cgaccttctt tgtgcttgga        1140
agcagagcgc aatattatcc cgaaacgata aaacggatgc tgaaggaagg aaacgaagtc        1200
ggcaaccatt cctgggacca tccgttattg acaaggctgt caaatgaaaa agcgtatcag        1260
gagattaacg acacgcaaga aatgatcgaa aaaatcagcg acacctgcc tgtacacttg         1320 cgtcctccat acgcgggat caatgattcc gtccgctcgc tttccaatct gaaggtttca         1380
ttgtgggatg ttgatccgga agattggaag tacaaaaata agcaaagat tgtcaatcat         1440 gtcatgagcc atgcgggaga cggaaaaatc gtcttaatgc acgatattta tgcaacgtcc        1500
gcagatgctg ctgaagagat tattaaaaag ctgaaagcaa aaggctatca attggtaact        1560
gtatctcagc ttgaagaagt gaagaagcag agaggctatt gaataaatga gtagaaagcg        1620
ccatatcggc gcttttcttt tggaagaaaa tatagggaaa atggtacttg ttaaaaattc        1680
ggaatattta tacaatatca tatgtatcac attgaaagga ggggcctgct gtccagactg        1740
tccgctgtgt aaaaaaagg aataaggggg ggttgacatt attttactga tatgtataat         1800
ataatttgta taagaaaatg gaggggccct cgaaacgtaa gatgaaacct tagataaaag        1860 tgctttttt gttgcaattg aagaattatt aatgttaagc ttaattaaag ataatatctt         1920
tgaattgtaa cgcccctcaa aagtaagaac tacaaaaaaa gaatacgtta tatagaaata        1980
tgtttgaacc ttcttcagat tacaaatata ttcggacgga ctctacctca aatgcttatc        2040
taactataga atgacataca agcacaacct tgaaaatttg aaaatataac taccaatgaa        2100
cttgttcatg tgaattatcg ctgtatttaa ttttctcaat tcaatatata atatgccaat        2160
acattgttac aagtagaaat taagacaccc ttgatagcct tactatacct aacatgatgt        2220
agtattaaat gaatatgtaa atatatttat gataagaagc gacttattta taatcattac        2280 atattttct attggaatga ttaagattcc aatagaatag tgtataaatt atttatcttg         2340
aaaggaggga tggctaaaaa cgaagaacat taaaaacata tatttgcacc gtctaatgga        2400
tttatgaaaa atcattttat cagtttgaaa attatgtatt atggccacat tgaaagggga       2460 ggagaatc atg aaa caa caa aaa cgg ctt tac gcc cga ttg ctg acg ctg        2510
         Met Lys Gln Gln Lys Arg Leu Tyr Ala Arg Leu Leu Thr Leu
                 -25                 -20 tta ttt gcg ctc atc ttc ttg ctg cct cat tct gca gca gcg gcg gta        2558
Leu Phe Ala Leu Ile Phe Leu Leu Pro His Ser Ala Ala Ala Ala Val
-15             -10              -5              -1  1 aat ggc acg ctg atg cag tat ttt gaa tgg tat acg ccg aac gac ggc        2606
Asn Gly Thr Leu Met Gln Tyr Phe Glu Trp Tyr Thr Pro Asn Asp Gly
            5                  10                 15 cag cat tgg aaa cga ttg cag aat gat gcg gaa cat tta tcg gat atc        2654
Gln His Trp Lys Arg Leu Gln Asn Asp Ala Glu His Leu Ser Asp Ile
        20                  25                  30 gga atc act gcc gtc tgg att cct ccc gca tac aaa gga ttg agc caa        2702
Gly Ile Thr Ala Val Trp Ile Pro Pro Ala Tyr Lys Gly Leu Ser Gln
    35                  40                  45 tcc gat aac gga tac gga cct tat gat ttg tat gat tta gga gaa ttc        2750
Ser Asp Asn Gly Tyr Gly Pro Tyr Asp Leu Tyr Asp Leu Gly Glu Phe
50                  55                  60                  65 cag caa aaa ggg acg gtc aga acg aaa tac ggc aca aaa tca gag ctt        2798
Gln Gln Lys Gly Thr Val Arg Thr Lys Tyr Gly Thr Lys Ser Glu Leu
                70                  75                  80 caa gat gcg atc ggc tca ctg cat tcc cgg aac gtc caa gta tac gga        2846
Gln Asp Ala Ile Gly Ser Leu His Ser Arg Asn Val Gln Val Tyr Gly
```

```
                        85                    90                    95
gat gtg gtt ttg aat cat aag gct ggt gct gat gca aca gaa gat gta      2894
Asp Val Val Leu Asn His Lys Ala Gly Ala Asp Ala Thr Glu Asp Val
        100                 105                 110 act gcc gtc gaa gtc aat ccg gcc aat aga aat cag gaa act tcg gag      2942
Thr Ala Val Glu Val Asn Pro Ala Asn Arg Asn Gln Glu Thr Ser Glu
115                 120                 125 gaa tat caa atc aaa gcg tgg acg gat ttt cgt ttt ccg ggc cgt gga      2990
Glu Tyr Gln Ile Lys Ala Trp Thr Asp Phe Arg Phe Pro Gly Arg Gly
130                 135                 140                 145 aac acg tac agt gat ttt aaa tgg cat tgg tat cat ttc gac gga gcg      3038
Asn Thr Tyr Ser Asp Phe Lys Trp His Trp Tyr His Phe Asp Gly Ala
                150                 155                 160 gac tgg gat gaa tcc cgg aag atc agc cgc atc ttt aag ttt cgt ggg      3086
Asp Trp Asp Glu Ser Arg Lys Ile Ser Arg Ile Phe Lys Phe Arg Gly
            165                 170                 175 gaa gga aaa gct tgg aat tgg gaa gta tca agt gaa aac ggc aac tat      3134
Glu Gly Lys Ala Trp Asn Trp Glu Val Ser Ser Glu Asn Gly Asn Tyr
        180                 185                 190 gac tat tta atg tat gct gat gtt gac tac gac cac cct gat gtc gtg      3182
Asp Tyr Leu Met Tyr Ala Asp Val Asp Tyr Asp His Pro Asp Val Val
195                 200                 205 gca gag aca aaa aaa tgg ggt atc tgg tat gcg aat gaa ctg tca tta      3230
Ala Glu Thr Lys Lys Trp Gly Ile Trp Tyr Ala Asn Glu Leu Ser Leu
210                 215                 220                 225 gac ggc ttc cgt att gat gcc gcc aaa cat att aaa ttt tca ttt ctg      3278
Asp Gly Phe Arg Ile Asp Ala Ala Lys His Ile Lys Phe Ser Phe Leu
                230                 235                 240 cgt gat tgg gtt cag gcg gtc aga cag gcg acg gga aaa gaa atg ttt      3326
Arg Asp Trp Val Gln Ala Val Arg Gln Ala Thr Gly Lys Glu Met Phe
            245                 250                 255 acg gtt gcg gag tat tgg cag aat aat gcc ggg aaa ctc gaa aac tac      3374
Thr Val Ala Glu Tyr Trp Gln Asn Asn Ala Gly Lys Leu Glu Asn Tyr
        260                 265                 270 ttg aat aaa aca agc ttt aat caa tcc gtg ttt gat gtt ccg ctt cat      3422
Leu Asn Lys Thr Ser Phe Asn Gln Ser Val Phe Asp Val Pro Leu His
275                 280                 285 ttc aat tta cag gcg gct tcc tca caa gga ggc gga tat gat atg agg      3470
Phe Asn Leu Gln Ala Ala Ser Ser Gln Gly Gly Gly Tyr Asp Met Arg
290                 295                 300                 305 cgt ttg ctg gac ggt acc gtt gtg tcc agg cat ccg gaa aag gcg gtt      3518
Arg Leu Leu Asp Gly Thr Val Val Ser Arg His Pro Glu Lys Ala Val
                310                 315                 320 aca ttt gtt gaa aat cat gac aca cag ccg gga cag tca ttg gaa tcg      3566
Thr Phe Val Glu Asn His Asp Thr Gln Pro Gly Gln Ser Leu Glu Ser
            325                 330                 335 aca gtc caa act tgg ttt aaa ccg ctt gca tac gcc ttt att ttg aca      3614
Thr Val Gln Thr Trp Phe Lys Pro Leu Ala Tyr Ala Phe Ile Leu Thr
        340                 345                 350 aga gaa tcc ggt tat cct cag gtg ttc tat ggg gat atg tac ggg aca      3662
Arg Glu Ser Gly Tyr Pro Gln Val Phe Tyr Gly Asp Met Tyr Gly Thr
355                 360                 365 aaa ggg aca tcg cca aag gaa att ccc tca ctg aaa gat aat ata gag      3710
Lys Gly Thr Ser Pro Lys Glu Ile Pro Ser Leu Lys Asp Asn Ile Glu
370                 375                 380                 385 ccg att tta aaa gcg cgt aag gag tac gca tac ggg ccc cag cac gat      3758
Pro Ile Leu Lys Ala Arg Lys Glu Tyr Ala Tyr Gly Pro Gln His Asp
                390                 395                 400 tat att gac cac ccg gat gtg atc gga tgg acg agg gaa ggt gac agc      3806
Tyr Ile Asp His Pro Asp Val Ile Gly Trp Thr Arg Glu Gly Asp Ser
```

| | | | | | | | | | | | | | | | |
|---|---|---|---|---|---|---|---|---|---|---|---|---|---|---|---|
| Tyr | Ile | Asp | His | Pro | Asp | Val | Ile | Gly | Trp | Thr | Arg | Glu | Gly | Asp | Ser |
| | | | 405 | | | | 410 | | | | 415 | | | | |

```
tcc gcc gcc aaa tca ggt ttg gcc gct tta atc acg gac gga ccc ggc    3854
Ser Ala Ala Lys Ser Gly Leu Ala Ala Leu Ile Thr Asp Gly Pro Gly
            420                 425                 430 gga tca aag cgg atg tat gcc ggc ctg aaa aat gcc ggc gag aca tgg    3902
Gly Ser Lys Arg Met Tyr Ala Gly Leu Lys Asn Ala Gly Glu Thr Trp
    435                 440                 445 tat gac ata acg ggc aac cgt tca gat act gta aaa atc gga tct gac    3950
Tyr Asp Ile Thr Gly Asn Arg Ser Asp Thr Val Lys Ile Gly Ser Asp
450                 455                 460                 465 ggc tgg gga gag ttt cat gta aac gat ggg tcc gtc tcc att tat gtt    3998
Gly Trp Gly Glu Phe His Val Asn Asp Gly Ser Val Ser Ile Tyr Val
                    470                 475                 480 cag aaa                                                            4054
Gln Lys
```

```
taacgcgtgc tagcggccgc gtcgactaga agagcagaga ggacggattt             4054
```

| | |
|---|---|
| cctgaaggaa atccgttttt ttattttgcc cgtcttataa atttcgttga gatctacgcg | 4114 |
| tccatgggct agcgcggccg cgtcgacagg cctctttgat tacattttat aattaatttt | 4174 |
| aacaaagtgt catcagccct caggaaggac ttgctgacag tttgaatcgc ataggtaagg | 4234 |
| cggggatgaa atggcaacgt tatctgatgt agcaaagaaa gcaaatgtgt cgaaaatgac | 4294 |
| ggtatcgcgg gtgatcaatc atcctgagac tgtgacggat gaattgaaaa agcttgttca | 4354 |
| ttccgcaatg aaggagctca attatatacc gaactatgca gcaagagcgc tcgttcaaaa | 4414 |
| cagaacacag gtcgtcaagc tgctcatact ggaagaaatg gatacaacag aaccttatta | 4474 |
| tatgaatctg ttaacgggaa tcagccgcga gctggaccgt catcattatg ctttgcagct | 4534 |
| tgtcacaagg aaatctctca atatcggcca gtgcgacggc attattgcga cggggttgag | 4594 |
| aaaagccgat tttgaagggc tcatcaaggt ttttgaaaag cctgtcgttg tattcgggca | 4654 |
| aaatgaaatg ggctacgatt ttattgatgt taacaatgaa aaaggaacct atatggcaac | 4714 |
| acgtcacgtc attggtctgg gcgtccgcaa tgtcgtcttt tttgggatcg atttggatga | 4774 |
| gccctttgaa cggtcaaggg aaaaaggcta ccttcaggcg atggaaggca gtctgaaaaa | 4834 |
| agcagcgatt ttccggatgg aaaacagttc aaaaaaaagt gaagcacgcg cgcgggaagt | 4894 |
| gcttgcatcc tttgacgcac ctgcagcggt tgtttgcgct tcggaccgaa tcgcgctcgg | 4954 |
| ggttatccgc gcggtgcaat cgcttggtaa aagaattccg gaagatgtcg cggtcaccgg | 5014 |
| ctatgacggg gtgtttctcg accggatcgc ttcgcctcgc ctgacaaccg tcagacagcc | 5074 |
| tgttgttgaa atgggagagg cttgcgcgag aatcctgctg aaaaaaatca atgaagacgg | 5134 |
| agcgccgcaa ggcaatcaat tttttgagcc ggagcttatt gtccgcgaat cgactttgta | 5194 |
| gggtgtctca ttctgttacc gttaacagct gaaaatgatt gttcctgtta ccgccgtcat | 5254 |
| gataatttca gaataaaagc cggtttatca cagccggaca accaaaaggg ggaaacatga | 5314 |
| tggaatatgc agcgatacat catcagcctt tcagctctga tgcctattct tacaatggac | 5374 |
| ggacattgca catcaagatc cgtacaaaaa aggatgatgc cgaacacgtc cgcttggttt | 5434 |
| ggggcgatcc ttacgaatac accggcggca catggaaagc gaacgagctt gcgatggcga | 5494 |
| aaattgccgc aacaagcacc catgattact ggtttgccga agtggcgcct ccattcaggc | 5554 |
| gtctgcaata cggatttatc ctgacaggcg ctgatgatcg agacactttt tacggaagca | 5614 |
| atggtgcatg tccgtttgcc g | 5635 |

```
<210> SEQ ID NO 15
<211> LENGTH: 512
```

<212> TYPE: PRT
<213> ORGANISM: Artificial sequence
<220> FEATURE:
<223> OTHER INFORMATION: Synthetic Construct

<400> SEQUENCE: 15

Met Lys Gln Gln Lys Arg Leu Tyr Ala Arg Leu Leu Thr Leu Leu Phe
                -25                 -20                 -15
Ala Leu Ile Phe Leu Leu Pro His Ser Ala Ala Ala Val Asn Gly
            -10                  -5              -1   1
Thr Leu Met Gln Tyr Phe Glu Trp Tyr Thr Pro Asn Asp Gly Gln His
      5                  10                  15
Trp Lys Arg Leu Gln Asn Asp Ala Glu His Leu Ser Asp Ile Gly Ile
 20                  25                  30                  35
Thr Ala Val Trp Ile Pro Pro Ala Tyr Lys Gly Leu Ser Gln Ser Asp
                 40                  45                  50
Asn Gly Tyr Gly Pro Tyr Asp Leu Tyr Asp Leu Gly Glu Phe Gln Gln
             55                  60                  65
Lys Gly Thr Val Arg Thr Lys Tyr Gly Thr Lys Ser Glu Leu Gln Asp
         70                  75                  80
Ala Ile Gly Ser Leu His Ser Arg Asn Val Gln Val Tyr Gly Asp Val
     85                  90                  95
Val Leu Asn His Lys Ala Gly Ala Asp Ala Thr Glu Asp Val Thr Ala
100                 105                 110                 115
Val Glu Val Asn Pro Ala Asn Arg Asn Gln Glu Thr Ser Glu Glu Tyr
                120                 125                 130
Gln Ile Lys Ala Trp Thr Asp Phe Arg Phe Pro Gly Arg Gly Asn Thr
            135                 140                 145
Tyr Ser Asp Phe Lys Trp His Trp Tyr His Phe Asp Gly Ala Asp Trp
        150                 155                 160
Asp Glu Ser Arg Lys Ile Ser Arg Ile Phe Lys Phe Arg Gly Glu Gly
    165                 170                 175
Lys Ala Trp Asn Trp Glu Val Ser Ser Glu Asn Gly Asn Tyr Asp Tyr
180                 185                 190                 195
Leu Met Tyr Ala Asp Val Asp Tyr Asp His Pro Asp Val Val Ala Glu
                200                 205                 210
Thr Lys Lys Trp Gly Ile Trp Tyr Ala Asn Glu Leu Ser Leu Asp Gly
            215                 220                 225
Phe Arg Ile Asp Ala Ala Lys His Ile Lys Phe Ser Phe Leu Arg Asp
        230                 235                 240
Trp Val Gln Ala Val Arg Gln Ala Thr Gly Lys Glu Met Phe Thr Val
    245                 250                 255
Ala Glu Tyr Trp Gln Asn Asn Ala Gly Lys Leu Glu Asn Tyr Leu Asn
260                 265                 270                 275
Lys Thr Ser Phe Asn Gln Ser Val Phe Asp Val Pro Leu His Phe Asn
                280                 285                 290
Leu Gln Ala Ala Ser Ser Gln Gly Gly Gly Tyr Asp Met Arg Arg Leu
            295                 300                 305
Leu Asp Gly Thr Val Val Ser Arg His Pro Glu Lys Ala Val Thr Phe
        310                 315                 320
Val Glu Asn His Asp Thr Gln Pro Gly Gln Ser Leu Glu Ser Thr Val
    325                 330                 335
Gln Thr Trp Phe Lys Pro Leu Ala Tyr Ala Phe Ile Leu Thr Arg Glu
340                 345                 350                 355

```
Ser Gly Tyr Pro Gln Val Phe Tyr Gly Asp Met Tyr Gly Thr Lys Gly
            360                 365                 370

Thr Ser Pro Lys Glu Ile Pro Ser Leu Lys Asp Asn Ile Glu Pro Ile
        375                 380                 385

Leu Lys Ala Arg Lys Glu Tyr Ala Tyr Gly Pro Gln His Asp Tyr Ile
            390                 395                 400

Asp His Pro Asp Val Ile Gly Trp Thr Arg Glu Gly Asp Ser Ser Ala
        405                 410                 415

Ala Lys Ser Gly Leu Ala Leu Ile Thr Asp Gly Pro Gly Gly Ser
420                 425                 430                 435

Lys Arg Met Tyr Ala Gly Leu Lys Asn Ala Gly Glu Thr Trp Tyr Asp
            440                 445                 450

Ile Thr Gly Asn Arg Ser Asp Thr Val Lys Ile Gly Ser Asp Gly Trp
        455                 460                 465

Gly Glu Phe His Val Asn Asp Gly Ser Val Ser Ile Tyr Val Gln Lys
            470                 475                 480
```

<210> SEQ ID NO 16
<211> LENGTH: 5635
<212> TYPE: DNA
<213> ORGANISM: Artificial sequence
<220> FEATURE:
<223> OTHER INFORMATION: DNA sequence of the B. licheniformis amyL region in AEB951.
<220> FEATURE:
<221> NAME/KEY: CDS
<222> LOCATION: (2469)..(4004)
<223> OTHER INFORMATION: Encoding mature FB024 with hybrid LQ2 signal peptide
<220> FEATURE:
<221> NAME/KEY: sig_peptide
<222> LOCATION: (2469)..(2555)
<220> FEATURE:
<221> NAME/KEY: mat_peptide
<222> LOCATION: (2556)..(4004)

<400> SEQUENCE: 16

```
tgatcttaaa aagagcgata tccgtttgga tgaacatacg gcattctatt atacaagcag    60
cggaatttca attgtatttc agcagtatga tatcgccccg tatgcagccg gaaaccagga   120
aataaagctt ccgtcgacgc ttttatatta gccccggcat tagatctaat atttgtaata   180
gaaacagaga gagcaagtca tgaaacagga gagtgagcag cgatgtctgg caaaccatca   240
tttcgatggg ttaaaatgtt gatttttta acgatattaa taggtttggc agggtactct   300
tacaataaag tgtcaagcaa cagccaagag cccctcagc caaaaaaga ccgcggacaa    360 tccggcctcg gcgtcgaatc catggtcaat gacagcaaac aagagaggta tgccatccat   420
tatccggtgt ttcacataaa agaaatcgat gaacaaataa aagattatgt gaatcaagaa   480
ttggccggtt ttaaagagga taacgcaaag gcccaggctc aggatgaaga cgggcctttt   540
gaactgaaca ttaaatataa ggttgtctat tatacaaagg atacggccag tgttgtgctg   600
aatcaataca tagaggccgg cggcgtatcg ggtacaacat ctgtcaagac gtttaacgct   660
gatttaaagc agaaaaagct gctgtcccct caagatctgt tgaagagaa ttcagatttt    720 ctgaacagga tttcaagcat tgcctatcag gaattgaaaa tcggaatcc gtctgctgac   780 atggctttat taaagaagg gacgagccct caggaagaac atttcagccg cttcgcgctt   840
cttgaaaacg aggtggaatt ttattttgag aaaaacaaa ccggtcttga acagtctgta   900 aaataaaaa aagaatgggt aaaagatatt ttaaagacc gatatcagga tatgaaaag    960 aatcgtcttc aggccaaacc tgatcaggag cctgttccgc ttccgaagca agcgaaaatt  1020
```

```
aatcccgatg aaaaagtgat tgccctcaca tttgatgacg gtccgaatcc cgctacaacg    1080
aataaaatat taaacgcttt acagaagcat gaagggcatg cgaccttctt tgtgcttgga    1140
agcagagcgc aatattatcc cgaaacgata aaacggatgc tgaaggaagg aaacgaagtc    1200
ggcaaccatt cctgggacca tccgttattg acaaggctgt caaatgaaaa agcgtatcag    1260
gagattaacg acacgcaaga aatgatcgaa aaaatcagcg acacctgcc tgtacacttg     1320
cgtcctccat acggcgggat caatgattcc gtccgctcgc tttccaatct gaaggtttca    1380
ttgtgggatg ttgatccgga agattggaag tacaaaaata agcaaagat tgtcaatcat     1440
gtcatgagcc atgcgggaga cggaaaaatc gtcttaatgc acgatattta tgcaacgtcc    1500
gcagatgctg ctgaagagat tattaaaaag ctgaaagcaa aaggctatca attggtaact    1560
gtatctcagc ttgaagaagt gaagaagcag agaggctatt gaataaatga gtagaaagcg    1620
ccatatcggc gcttttcttt tggaagaaaa tatagggaaa atggtacttg ttaaaaattc    1680
ggaatattta tacaatatca tatgtatcac attgaaagga ggggcctgct gtccagactg    1740
tccgctgtgt aaaaaaaagg aataaagggg ggttgacatt atttactga tatgtataat      1800
ataatttgta taagaaatg gaggggccct cgaaacgtaa gatgaaacct tagataaaag     1860
tgcttttttt gttgcaattg aagaattatt aatgttaagc ttaattaaag ataatatctt    1920
tgaattgtaa cgcccctcaa aagtaagaac tacaaaaaaa gaatacgtta tatagaaata    1980
tgtttgaacc ttcttcagat tacaaatata ttcggacgga ctctacctca aatgcttatc    2040
taactataga atgacataca agcacaacct tgaaaatttg aaaatataac taccaatgaa    2100
cttgttcatg tgaattatcg ctgtatttaa ttttctcaat tcaatatata atatgccaat    2160
acattgttac aagtagaaat taagacaccc ttgatagcct tactatacct aacatgatgt    2220
agtattaaat gaatatgtaa atatatttat gataagaagc gacttattta taatcattac    2280
atattttctt attggaatga ttaagattcc aatagaatag tgtataaatt atttatcttg    2340
aaaggaggga tggctaaaaa cgaagaacat taaaaacata tatttgcacc gtctaatgga    2400
tttatgaaaa atcattttat cagtttgaaa attatgtatt atggccacat tgaaaggga     2460
ggagaatc atg aaa caa caa aaa cgg ctt tac gcc cga ttg gtg ctt atg     2510
          Met Lys Gln Gln Lys Arg Leu Tyr Ala Arg Leu Val Leu Met
              -25                  -20
tgc acg ctg tta ttt gtc agt ttg ccg att aca aaa aca tca gcc gta      2558
Cys Thr Leu Leu Phe Val Ser Leu Pro Ile Thr Lys Thr Ser Ala Val
-15                 -10                  -5              -1  1
aat ggc acg ctg atg cag tat ttt gaa tgg tat acg ccg aac gac ggc      2606
Asn Gly Thr Leu Met Gln Tyr Phe Glu Trp Tyr Thr Pro Asn Asp Gly
        5                   10                  15
cag cat tgg aaa cga ttg cag aat gat gcg gaa cat tta tcg gat atc      2654
Gln His Trp Lys Arg Leu Gln Asn Asp Ala Glu His Leu Ser Asp Ile
        20                  25                  30
gga atc act gcc gtc tgg att cct ccc gca tac aaa gga ttg agc caa      2702
Gly Ile Thr Ala Val Trp Ile Pro Pro Ala Tyr Lys Gly Leu Ser Gln
        35                  40                  45
tcc gat aac gga tac gga cct tat gat ttg tat gat tta gga gaa ttc      2750
Ser Asp Asn Gly Tyr Gly Pro Tyr Asp Leu Tyr Asp Leu Gly Glu Phe
50                  55                  60                  65
cag caa aaa ggg acg gtc aga acg aaa tac ggc aca aaa tca gag ctt      2798
Gln Gln Lys Gly Thr Val Arg Thr Lys Tyr Gly Thr Lys Ser Glu Leu
            70                  75                  80
caa gat gcg atc ggc tca ctg cat tcc cgg aac gtc caa gta tac gga      2846
Gln Asp Ala Ile Gly Ser Leu His Ser Arg Asn Val Gln Val Tyr Gly
```

-continued

| | | | | | | | | | | | | | | | | |
|---|---|---|---|---|---|---|---|---|---|---|---|---|---|---|---|---|
| | | | | 85 | | | | | 90 | | | | | 95 | | |

```
gat gtg gtt ttg aat cat aag gct ggt gct gat gca aca gaa gat gta    2894
Asp Val Val Leu Asn His Lys Ala Gly Ala Asp Ala Thr Glu Asp Val
        100                 105                 110 act gcc gtc gaa gtc aat ccg gcc aat aga aat cag gaa act tcg gag    2942
Thr Ala Val Glu Val Asn Pro Ala Asn Arg Asn Gln Glu Thr Ser Glu
    115                 120                 125 gaa tat caa atc aaa gcg tgg acg gat ttt cgt ttt ccg ggc cgt gga    2990
Glu Tyr Gln Ile Lys Ala Trp Thr Asp Phe Arg Phe Pro Gly Arg Gly
130                 135                 140                 145 aac acg tac agt gat ttt aaa tgg cat tgg tat cat ttc gac gga gcg    3038
Asn Thr Tyr Ser Asp Phe Lys Trp His Trp Tyr His Phe Asp Gly Ala
                150                 155                 160 gac tgg gat gaa tcc cgg aag atc agc cgc atc ttt aag ttt cgt ggg    3086
Asp Trp Asp Glu Ser Arg Lys Ile Ser Arg Ile Phe Lys Phe Arg Gly
            165                 170                 175 gaa gga aaa gct tgg aat tgg gaa gta tca agt gaa aac ggc aac tat    3134
Glu Gly Lys Ala Trp Asn Trp Glu Val Ser Ser Glu Asn Gly Asn Tyr
        180                 185                 190 gac tat tta atg tat gct gat gtt gac tac gac cac cct gat gtc gtg    3182
Asp Tyr Leu Met Tyr Ala Asp Val Asp Tyr Asp His Pro Asp Val Val
    195                 200                 205 gca gag aca aaa aaa tgg ggt atc tgg tat gcg aat gaa ctg tca tta    3230
Ala Glu Thr Lys Lys Trp Gly Ile Trp Tyr Ala Asn Glu Leu Ser Leu
210                 215                 220                 225 gac ggc ttc cgt att gat gcc gcc aaa cat att aaa ttt tca ttt ctg    3278
Asp Gly Phe Arg Ile Asp Ala Ala Lys His Ile Lys Phe Ser Phe Leu
                230                 235                 240 cgt gat tgg gtt cag gcg gtc aga cag gcg acg gga aaa gaa atg ttt    3326
Arg Asp Trp Val Gln Ala Val Arg Gln Ala Thr Gly Lys Glu Met Phe
            245                 250                 255 acg gtt gcg gag tat tgg cag aat aat gcc ggg aaa ctc gaa aac tac    3374
Thr Val Ala Glu Tyr Trp Gln Asn Asn Ala Gly Lys Leu Glu Asn Tyr
        260                 265                 270 ttg aat aaa aca agc ttt aat caa tcc gtg ttt gat gtt ccg ctt cat    3422
Leu Asn Lys Thr Ser Phe Asn Gln Ser Val Phe Asp Val Pro Leu His
    275                 280                 285 ttc aat tta cag gcg gct tcc tca caa gga ggc gga tat gat atg agg    3470
Phe Asn Leu Gln Ala Ala Ser Ser Gln Gly Gly Gly Tyr Asp Met Arg
290                 295                 300                 305 cgt ttg ctg gac ggt acc gtt gtg tcc agg cat ccg gaa aag gcg gtt    3518
Arg Leu Leu Asp Gly Thr Val Val Ser Arg His Pro Glu Lys Ala Val
                310                 315                 320 aca ttt gtt gaa aat cat gac aca cag ccg gga cag tca ttg gaa tcg    3566
Thr Phe Val Glu Asn His Asp Thr Gln Pro Gly Gln Ser Leu Glu Ser
            325                 330                 335 aca gtc caa act tgg ttt aaa ccg ctt gca tac gcc ttt att ttg aca    3614
Thr Val Gln Thr Trp Phe Lys Pro Leu Ala Tyr Ala Phe Ile Leu Thr
        340                 345                 350 aga gaa tcc ggt tat cct cag gtg ttc tat ggg gat atg tac ggg aca    3662
Arg Glu Ser Gly Tyr Pro Gln Val Phe Tyr Gly Asp Met Tyr Gly Thr
    355                 360                 365 aaa ggg aca tcg cca aag gaa att ccc tca ctg aaa gat aat ata gag    3710
Lys Gly Thr Ser Pro Lys Glu Ile Pro Ser Leu Lys Asp Asn Ile Glu
370                 375                 380                 385 ccg att tta aaa gcg cgt aag gag tac gca tac ggg ccc cag cac gat    3758
Pro Ile Leu Lys Ala Arg Lys Glu Tyr Ala Tyr Gly Pro Gln His Asp
                390                 395                 400 tat att gac cac ccg gat gtg atc gga tgg acg agg gaa ggt gac agc    3806
```

| | | | | | | | | | | | | | | |
|---|---|---|---|---|---|---|---|---|---|---|---|---|---|---|
| Tyr | Ile | Asp | His | Pro | Asp | Val | Ile | Gly | Trp | Thr | Arg | Glu | Gly | Asp | Ser |
| | | | 405 | | | | 410 | | | | 415 | | | | |

```
tcc gcc gcc aaa tca ggt ttg gcc gct tta atc acg gac gga ccc ggc      3854
Ser Ala Ala Lys Ser Gly Leu Ala Ala Leu Ile Thr Asp Gly Pro Gly
            420                 425                 430 gga tca aag cgg atg tat gcc ggc ctg aaa aat gcc ggc gag aca tgg      3902
Gly Ser Lys Arg Met Tyr Ala Gly Leu Lys Asn Ala Gly Glu Thr Trp
        435                 440                 445 tat gac ata acg ggc aac cgt tca gat act gta aaa atc gga tct gac      3950
Tyr Asp Ile Thr Gly Asn Arg Ser Asp Thr Val Lys Ile Gly Ser Asp
450                 455                 460                 465 ggc tgg gga gag ttt cat gta aac gat ggg tcc gtc tcc att tat gtt      3998
Gly Trp Gly Glu Phe His Val Asn Asp Gly Ser Val Ser Ile Tyr Val
                470                 475                 480 cag aaa taacgcgtgc tagcggccgc gtcgactaga agagcagaga ggacggattt      4054
Gln Lys cctgaaggaa atccgttttt ttattttgcc cgtcttataa atttcgttga gatctacgcg   4114
tccatgggct agcgcggccg cgtcgacagg cctctttgat tacattttat aattaatttt   4174
aacaaagtgt catcagccct caggaaggac ttgctgacag tttgaatcgc ataggtaagg   4234
cggggatgaa atgcaacgt tatctgatgt agcaaagaaa gcaaatgtgt cgaaaatgac    4294
ggtatcgcgg gtgatcaatc atcctgagac tgtgacggat gaattgaaaa agcttgttca   4354
ttccgcaatg aaggagctca attatatacc gaactatgca gcaagagcgc tcgttcaaaa   4414
cagaacacag gtcgtcaagc tgctcatact ggaagaaatg gatacaacag aaccttatta   4474
tatgaatctg ttaacgggaa tcagccgcga gctggaccgt catcattatg ctttgcagct   4534
tgtcacaagg aaatctctca atatcggcca gtgcgacggc attattgcga cggggttgag   4594
aaaagccgat tttgaagggc tcatcaaggt ttttgaaaag cctgtcgttg tattcgggca   4654
aaatgaaatg ggctacgatt ttattgatgt taacaatgaa aaaggaacct atatggcaac   4714
acgtcacgtc attggtctgg gcgtccgcaa tgtcgtcttt tttgggatcg atttggatga   4774 gcccttgaa cggtcaaggg aaaaaggcta ccttcaggcg atggaaggca gtctgaaaaa    4834
agcagcgatt ttccggatgg aaaacagttc aaaaaaaagt gaagcacgcg cgcgggaagt   4894
gcttgcatcc tttgacgcac ctgcagcggt tgtttgcgct tcggaccgaa tcgcgctcgg   4954
ggttatccgc gcggtgcaat cgcttggtaa aagaattccg gaagatgtcg cggtcaccgg   5014
ctatgacggg gtgtttctcg accggatcgc ttcgcctcgc ctgacaaccg tcagacagcc   5074
tgttgttgaa atgggagagg cttgcgcgag aatcctgctg aaaaaaatca atgaagacgg   5134
agcgccgcaa ggcaatcaat ttttgagcc ggagcttatt gtccgcgaat cgactttgta    5194
gggtgtctca ttctgttacc gttaacagct gaaaatgatt gttcctgtta ccgccgtcat   5254
gataatttca gaataaaagc cggtttatca cagccggaca accaaagggg gaaacatga    5314 tggaatatgc agcgatacat catcagcctt tcagctctga tgcctattct tacaatggac   5374
ggacattgca catcaagatc cgtacaaaaa aggatgatgc cgaacacgtc cgcttggttt   5434
ggggcgatcc ttacgaatac accggcggca catggaaagc gaacgagctt gcgatggcga   5494
aaattgccgc aacaagcacc catgattact ggtttgccga agtggcgcct ccattcaggc   5554
gtctgcaata cggatttatc ctgacaggcg ctgatgatcg agacactttt tacggaagca   5614
atggtgcatg tccgtttgcc g                                             5635
```

<210> SEQ ID NO 17
<211> LENGTH: 512

```
<212> TYPE: PRT
<213> ORGANISM: Artificial sequence
<220> FEATURE:
<223> OTHER INFORMATION: Synthetic Construct

<400> SEQUENCE: 17
```

Met Lys Gln Gln Lys Arg Leu Tyr Ala Arg Leu Val Leu Met Cys Thr
                -25                 -20                 -15

Leu Leu Phe Val Ser Leu Pro Ile Thr Lys Thr Ser Ala Val Asn Gly
            -10                  -5              -1   1

Thr Leu Met Gln Tyr Phe Glu Trp Tyr Thr Pro Asn Asp Gly Gln His
         5                  10                  15

Trp Lys Arg Leu Gln Asn Asp Ala Glu His Leu Ser Asp Ile Gly Ile
 20                  25                  30                  35

Thr Ala Val Trp Ile Pro Pro Ala Tyr Lys Gly Leu Ser Gln Ser Asp
                 40                  45                  50

Asn Gly Tyr Gly Pro Tyr Asp Leu Tyr Asp Leu Gly Glu Phe Gln Gln
             55                  60                  65

Lys Gly Thr Val Arg Thr Lys Tyr Gly Thr Lys Ser Glu Leu Gln Asp
         70                  75                  80

Ala Ile Gly Ser Leu His Ser Arg Asn Val Gln Val Tyr Gly Asp Val
         85                  90                  95

Val Leu Asn His Lys Ala Gly Ala Asp Ala Thr Glu Asp Val Thr Ala
100                 105                 110                 115

Val Glu Val Asn Pro Ala Asn Arg Asn Gln Glu Thr Ser Glu Glu Tyr
                120                 125                 130

Gln Ile Lys Ala Trp Thr Asp Phe Arg Phe Pro Gly Arg Gly Asn Thr
            135                 140                 145

Tyr Ser Asp Phe Lys Trp His Trp Tyr His Phe Asp Gly Ala Asp Trp
            150                 155                 160

Asp Glu Ser Arg Lys Ile Ser Arg Ile Phe Lys Phe Arg Gly Glu Gly
            165                 170                 175

Lys Ala Trp Asn Trp Glu Val Ser Ser Glu Asn Gly Asn Tyr Asp Tyr
180                 185                 190                 195

Leu Met Tyr Ala Asp Val Asp Tyr Asp His Pro Asp Val Val Ala Glu
                200                 205                 210

Thr Lys Lys Trp Gly Ile Trp Tyr Ala Asn Glu Leu Ser Leu Asp Gly
            215                 220                 225

Phe Arg Ile Asp Ala Ala Lys His Ile Lys Phe Ser Phe Leu Arg Asp
            230                 235                 240

Trp Val Gln Ala Val Arg Gln Ala Thr Gly Lys Glu Met Phe Thr Val
            245                 250                 255

Ala Glu Tyr Trp Gln Asn Asn Ala Gly Lys Leu Glu Asn Tyr Leu Asn
260                 265                 270                 275

Lys Thr Ser Phe Asn Gln Ser Val Phe Asp Val Pro Leu His Phe Asn
                280                 285                 290

Leu Gln Ala Ala Ser Ser Gln Gly Gly Gly Tyr Asp Met Arg Arg Leu
            295                 300                 305

Leu Asp Gly Thr Val Val Ser Arg His Pro Glu Lys Ala Val Thr Phe
            310                 315                 320

Val Glu Asn His Asp Thr Gln Pro Gly Gln Ser Leu Glu Ser Thr Val
            325                 330                 335

Gln Thr Trp Phe Lys Pro Leu Ala Tyr Ala Phe Ile Leu Thr Arg Glu
340                 345                 350                 355

-continued

```
Ser Gly Tyr Pro Gln Val Phe Tyr Gly Asp Met Tyr Gly Thr Lys Gly
                360                 365                 370

Thr Ser Pro Lys Glu Ile Pro Ser Leu Lys Asp Asn Ile Glu Pro Ile
            375                 380                 385

Leu Lys Ala Arg Lys Glu Tyr Ala Tyr Gly Pro Gln His Asp Tyr Ile
        390                 395                 400

Asp His Pro Asp Val Ile Gly Trp Thr Arg Glu Gly Asp Ser Ser Ala
    405                 410                 415

Ala Lys Ser Gly Leu Ala Ala Leu Ile Thr Asp Gly Pro Gly Gly Ser
420                 425                 430                 435

Lys Arg Met Tyr Ala Gly Leu Lys Asn Ala Gly Glu Thr Trp Tyr Asp
                440                 445                 450

Ile Thr Gly Asn Arg Ser Asp Thr Val Lys Ile Gly Ser Asp Gly Trp
            455                 460                 465

Gly Glu Phe His Val Asn Asp Gly Ser Val Ser Ile Tyr Val Gln Lys
                470                 475                 480
```